United States Patent
Sivan et al.

(10) Patent No.: US 10,370,630 B2
(45) Date of Patent: *Aug. 6, 2019

(54) METHOD AND APPARATUS FOR CELL ISOLATION, GROWTH, REPLICATION, MANIPULATION, AND ANALYSIS

(71) Applicant: TECHNION RESEARCH & DEVELOPMENT FOUNDATION LIMITED, Haifa (IL)

(72) Inventors: Uri Sivan, Haifa (IL); Elad Brod, Haifa (IL)

(73) Assignee: Technion Research & Development Foundation Limited (IL)

( * ) Notice: Subject to any disclaimer, the term of this patent is extended or adjusted under 35 U.S.C. 154(b) by 18 days.

This patent is subject to a terminal disclaimer.

(21) Appl. No.: 15/117,933

(22) PCT Filed: Feb. 10, 2015

(86) PCT No.: PCT/IL2015/050156
§ 371 (c)(1),
(2) Date: Aug. 10, 2016

(87) PCT Pub. No.: WO2015/118551
PCT Pub. Date: Aug. 13, 2015

(65) Prior Publication Data
US 2016/0348050 A1    Dec. 1, 2016

Related U.S. Application Data

(60) Provisional application No. 61/937,689, filed on Feb. 10, 2014.

(51) Int. Cl.
*C12M 1/32* (2006.01)
*B01L 3/00* (2006.01)
(Continued)

(52) U.S. Cl.
CPC .......... *C12M 23/12* (2013.01); *B01L 3/5027* (2013.01); *B01L 3/50273* (2013.01);
(Continued)

(58) Field of Classification Search
CPC ...... C12M 21/08; C12M 23/12; C12M 23/16; C12M 29/00; C12M 41/48; C12M 47/02;
(Continued)

(56) References Cited

U.S. PATENT DOCUMENTS 7,133,717 B2    11/2006    Coston et al.
2009/0098541 A1*    4/2009    Southern ........... B01L 3/502753
435/6.11
(Continued)

FOREIGN PATENT DOCUMENTS

WO    2007/022026 A2    2/2007
WO    2007/025883 A1    2/2007
(Continued)

OTHER PUBLICATIONS

Hashimshony, Tamar et al. "CEL-Seq: Single-cell RNA-Seq by Multiplexed linear Amplification" Cell Reports (2012), vol. 2, pp. 666-673.
(Continued)

*Primary Examiner* — Gailene Gabel
(74) *Attorney, Agent, or Firm* — McDonnell Boehnen Hulbert & Berghoff LLP

(57) ABSTRACT

According to an aspect of some embodiments, an apparatus for isolation and cytometric analysis of cells from a liquid medium is provided. The apparatus comprises a cell reservoir, for receiving a liquid medium containing a suspension of cells. The apparatus further comprises a cell cage array between the cell reservoir and an enclosed reservoir, each cell cage comprising a large opening adjacent to the first cell reservoir, a cell cage, and one or more small opening
(Continued)

adjacent to the enclosed reservoir. A connected liquid medium pump may move the suspended cells into cell cages by flowing the liquid medium from the cell reservoir to the enclosed reservoir. The apparatus further comprises a mechanical element which when actuated, pushes the cell cage array against a gel layer, forming a contiguous barrier to isolate each cell in a cell cage, and allowing cytometric analysis of isolated cells.

24 Claims, 19 Drawing Sheets

(51) Int. Cl.
    *C12M 1/00*     (2006.01)
    *C12M 3/00*     (2006.01)
    *C12M 3/06*     (2006.01)
    *C12M 1/36*     (2006.01)
    *G01N 33/569*     (2006.01)

(52) U.S. Cl.
    CPC ..... *B01L 3/50857* (2013.01); *B01L 3/502753* (2013.01); *C12M 21/08* (2013.01); *C12M 23/16* (2013.01); *C12M 29/00* (2013.01); *C12M 41/48* (2013.01); *C12M 47/02* (2013.01); *G01N 33/56966* (2013.01); *B01L 2300/069* (2013.01); *B01L 2300/0645* (2013.01); *B01L 2300/0681* (2013.01); *B01L 2300/0819* (2013.01); *B01L 2300/0829* (2013.01); *B01L 2400/049* (2013.01); *B01L 2400/0487* (2013.01)

(58) Field of Classification Search
    CPC ........... G01N 33/56966; B01L 3/50273; B01L 3/502753; B01L 3/50857; B01L 3/5027
    See application file for complete search history.

(56) References Cited

U.S. PATENT DOCUMENTS

| | | |
|---|---|---|
| 2011/0108422 A1 | 5/2011 | Heller et al. |
| 2011/0111981 A1 | 5/2011 | Love et al. |
| 2012/0156675 A1* | 6/2012 | Lueerssen ........... B01L 3/50853 435/6.11 |
| 2012/0224053 A1 | 9/2012 | Vykoukal et al. |
| 2014/0065704 A1 | 3/2014 | Shirai |
| 2014/0066318 A1 | 3/2014 | Frisen et al. |
| 2018/0023128 A1* | 1/2018 | Yanai ................... C12Q 1/6837 |

FOREIGN PATENT DOCUMENTS

| | | |
|---|---|---|
| WO | 2010/142954 A1 | 12/2010 |
| WO | 2012/048341 A1 | 4/2012 |
| WO | 2012/139209 A1 | 10/2012 |
| WO | 2012/141157 A1 | 10/2012 |
| WO | 2012/162779 A1 | 12/2012 |
| WO | 2013/180567 A2 | 12/2013 |
| WO | 2013/188872 A1 | 12/2013 |
| WO | 2014/137193 A1 | 12/2014 |
| WO | 2014/201273 A1 | 12/2014 |

OTHER PUBLICATIONS

The International Search Report (ISR) for PCT/IL2015/050156 dated May 31, 2015, pp. 1-4.
Written Opinion of the International Searching Authority for PCT/IL2015/050156 dated Jun. 2, 2015, pp. 1-6.

* cited by examiner

METHOD AND APPARATUS FOR CELL ISOLATION, GROWTH, REPLICATION, MANIPULATION, AND ANALYSIS

BACKGROUND

The present invention, in some embodiments thereof, relates to cytometry and, more particularly, but not exclusively, to cell isolation, immobilization, culture, manipulation, and analysis.

Flow cytometry has proven useful in analysis of living cells, where the cells may be inspected individually after antibody binding by flowing them serially through a detector. Other technologies may be based on the ability of a non-uniform electric field to exert forces on neutral, polarizable particles, such as cells, that are suspended in a liquid. This electrokinetic principle, called dielectrophoresis (DEP), is used to trap cells in DEP "cages" by creating an electric field above a subset of electrodes in an array that is in counter phase with the electric field of adjacent electrodes. When a DEP cage is moved by a change in the electric field pattern, the trapped cell moves with it.

SUMMARY

According to an aspect of some embodiments of the present invention there is provided an apparatus for isolation and cytometric analysis of cells from a liquid medium. The apparatus comprises a cell cage array between the cell reservoir and an enclosed reservoir, each cell cage comprising a large opening adjacent to the first cell reservoir, a cell enclosure, and one or more small opening adjacent to the enclosed reservoir. The apparatus further comprises the enclosed reservoir, for receiving the liquid medium through the cell cage array from the cell reservoir. The apparatus further comprises a liquid medium pump connected to the enclosed reservoir to move the suspended cells into the cell enclosures by flowing the liquid medium from the cell reservoir through the cell cage array to the enclosed reservoir.

Optionally, the apparatus further comprises a mechanical element which when actuated, pushes the cell cage array against a gel layer, thereby the gel layer forming a contiguous barrier to the large openings, isolating each cell in each of the cell enclosures, and allowing cytometric analysis of isolated cells.

Optionally, the apparatus further comprises a cell reservoir, for containing said liquid medium comprising said suspension of cells.

Optionally, the cell cage array is detachable from said apparatus and wherein said cell cage array is a single-use cell cage array.

According to an aspect of some embodiments of the present invention there is provided a disposable cell cage array comprising at least 100 cell cages, wherein each cell cage comprises a large opening on one side, a cell enclosure, and at least one small opening on the opposite side.

Optionally, the disposable cell cage array comprises at least 10,000 cell cages.

Optionally, the apparatus further comprises one or more first electrode, in electric contact with the liquid medium in the cell reservoir.

Optionally, the apparatus further comprises a semipermeable membrane between the enclosed reservoir and an ion reservoir.

Optionally, the apparatus further comprises an ion reservoir containing an ionic fluid.

Optionally, the apparatus further comprises one or more second electrode, in electric contact with the ionic fluid, such that a current flowing between the one or more first and second electrodes inject ions into the cell cages.

Optionally, the semipermeable membrane is any from a list comprising a cation exchange membrane (CEM), a charge mosaic membrane (CMM), a bipolar membrane (BPM), an anion exchange membrane (AEM), an alkali anion exchange membrane (AAEM), proton exchange membrane (PEM), and the like.

Optionally, the one or more first electrode is in electric contact with the liquid medium on one side of the enclosed reservoir, and the second electrode is in electric contact with the liquid medium on the opposite side of the enclosed reservoir, such that ion injection into cell cages is by diffusion.

Optionally, each of the cell enclosures has internal dimensions so that one or more cell fits in each cell enclosure, the large opening has dimensions large enough for the cell to enter the cell enclosure, and the small openings has dimensions smaller than the cell, prohibiting the cells from exiting the cell cage into the enclosed reservoir.

Optionally, the cell enclosures have internal dimensions so that two or more cells fit in each cell enclosure, and wherein the small openings are two or more small openings each adapted to receive a single cell.

Optionally, the cell enclosures have an internal shape of a target cell to isolate.

Optionally, the cell enclosures have an internal cylindrical shape.

Optionally, the cell enclosures have an internal conical shape.

Optionally, the cell enclosures have an internal hemispherical shape.

Optionally, the cell enclosures have internal dimensions large enough to fit a plurality of individual cells.

Optionally, the liquid medium pump is any device from the list of an electrical pump, a micropump, a manual syringe with attached caliper, an automatic programmable syringe, a computerized syringe, a syringe driver, a syringe pump, a programmable syringe pump, a media dispenser, an inductive pump, a pressure injection cell dispenser, a peristaltic pump, an infusion pump, and the like.

Optionally, between the cell cage array and the enclosed reservoir there is a glass, Polyethylene, and the like array support structure , such that the array support structure maintains the cell cage array in a substantially flat plane.

Optionally, the cell cage array is visible through an opaque window in the apparatus.

Optionally, the cell cage array further comprises attached antibodies.

Optionally, the gel layer further comprises attached antibodies.

Optionally, the apparatus further comprises a diffusing gel layer between the cell cage array and the enclosed reservoir.

Optionally, the apparatus further comprises an adsorbing layer adjacent to the gel layer, and the adsorbing layer is composed of any from the list of nitrocellulose, polyvinylidene difluoride (PVDF), low fluorescence PVDF and the like.

Optionally, the gel layer is composed of any from the list of agarose, acrylamide, bisacrylamide mixtures, and the like.

Optionally, the mechanical element is any element from the list of screw, level, step motor, step motor, computerized step motor, linear actuator, computerized linear actuator, and the like.

Optionally, the apparatus is a computerized apparatus comprising one or more user interface, one or more component interface, and one or more processing unit capable of controlling one or more component.

According to an aspect of some embodiments of the present invention there is provided a method for outputting results of cytometric analysis of isolated cells.

The method comprises receiving a liquid medium containing a suspension of cells to be analyzed into a cell reservoir. The method further comprises pumping the liquid medium from an enclosed reservoir, which is separated from the cell reservoir by a cell cage array, until isolated cells enter into the cell enclosures. The method further comprises moving a gel layer adjacent to the cell cage array, isolating the suspended cells one each in the cell enclosures to produce isolated cells. The method further comprises performing a cytometric analysis of the isolated cells. The method further comprises outputting results of the cytometric analysis.

Optionally, the method further comprises injecting ions into the cell cages by applying an electrical current through the liquid medium and cell cages, where the current flows between a first electrode in electric contact with the liquid medium in cell reservoir and a second electrode in electric contact with an ionic fluid in an ion reservoir which is separated from the enclosed reservoir by a semipermeable membrane, thus moving ions contained in the ionic fluid into the cell cages.

Optionally, the first electrode also comprises an ionic fluid in an ion reservoir and a semipermeable membrane, such that the semipermeable membrane controls ion injection from the first electrode.

Optionally, the ions are hydroxyl ions, thereby causing a change in pH and salt environment of the isolated cells and lysing the isolated cell.

Optionally, the cytometric analysis of the isolated cells includes introducing a chemical into the enclosed reservoir and the chemical enters the cell cages by diffusion.

Optionally, the cytometric analysis of the isolated cells includes electroporation of the isolated cells to introduce a chemical into a cytoplasm of the isolated cells.

Optionally, the method further comprises injecting ions into the cell cages by applying an electrical current through the liquid medium in the enclosed reservoir, where the current flows between a first electrode in electric contact with an ionic fluid in an ion reservoir which is separated from the enclosed reservoir by a semipermeable membrane and a second electrode in electric contact with the liquid medium in enclosed reservoir, thus moving ions contained in the ionic fluid into the cell cages by diffusion.

Optionally, the second electrode also comprises a second ionic fluid in a second ion reservoir and a second semipermeable membrane, such that the semipermeable membrane also controls ion injection from the second electrode in addition to the first electrode.

Optionally, the cytometric analysis includes imaging through an opaque side of the cell cage array.

Optionally, the pumping of the liquid medium stops when a sufficient number of cells have been isolated in the cell enclosures by monitoring a rate of flow of the liquid medium using the pumping.

Optionally, the cytometric analysis of the isolated cells includes any actions from a list comprising culturing, applying stimuli, immunocytochemical analysis, western blot, gel electrophoresis, protein purification, green fluorescent protein, protein immunostaining, protein sequencing, protein electrophoresis, protein immunoprecipitation, peptide mass fingerprinting, dual polarization interferometry, microscale thermophoresis, chromatin immunoprecipitation, surface plasmon resonance, nucleic acid analysis, optical analysis, protein analysis, fluorescent image analysis, cytophotometry, electroporation, genomics, transcriptomics, proteomics, metabolomics, spectrophotometery, and the like.

Optionally, during the pumping the cell cage array is transferred with isolated cells to a new liquid medium.

Optionally, the isolated cells in the cell cage array are proliferated to produce clusters of isolated cells in each cell enclosures, and some cells of each of cluster are transferred to one or more new cell cage arrays by a second pumping action.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention may involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DETAILED DESCRIPTION

Figure 1:
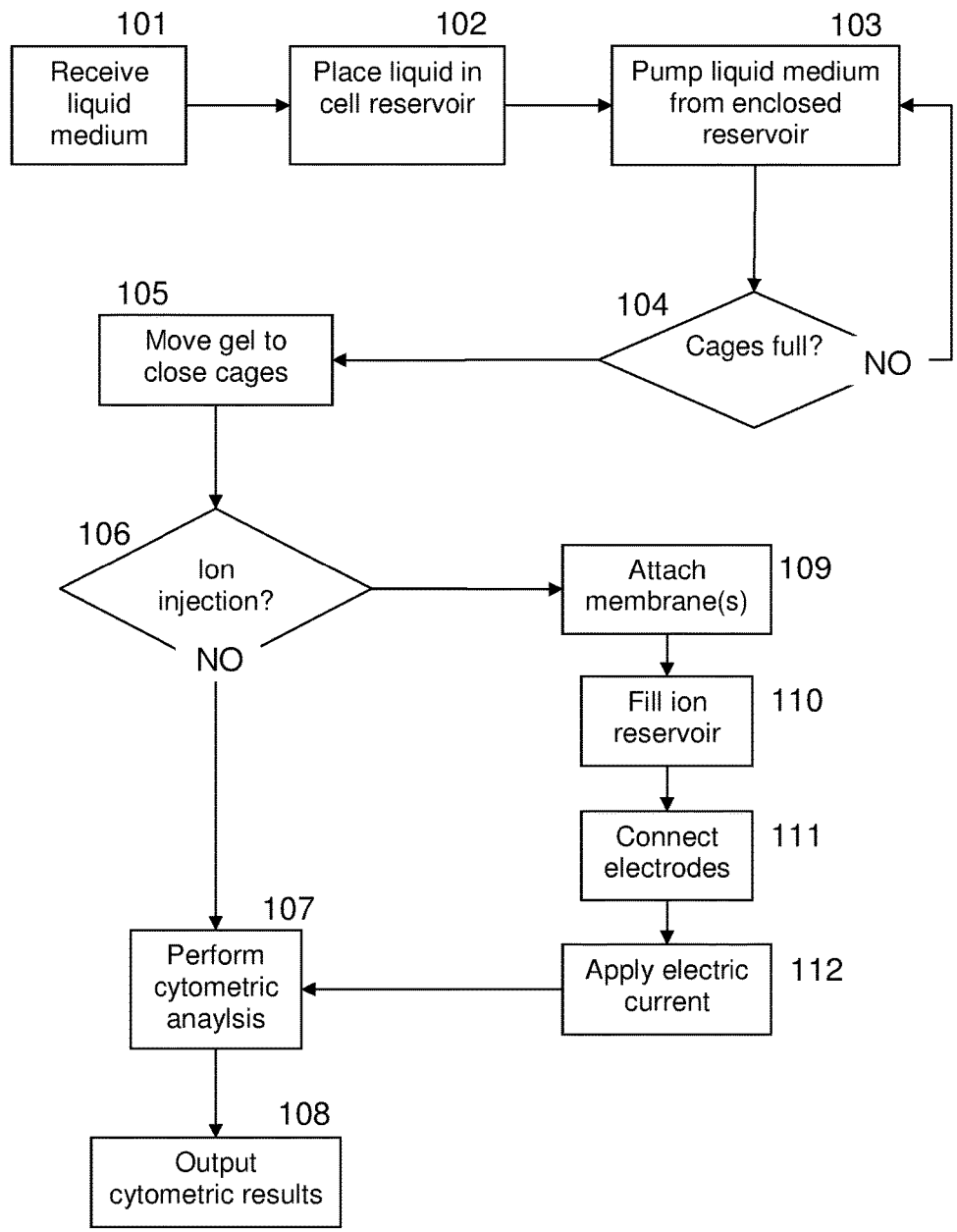
FIG. 1 is a flowchart of a method for trapping individual cells in cages and performing cytometric analysis to each individual cell, according to some embodiments of the invention.

The present invention, in some embodiments thereof, relates to cytometry and, more particularly, but not exclusively, to cell isolation, immobilization, culture, manipulation, and analysis.

In flow cytometry, there may be several disadvantages. As cells flows through the detector only once, this technique may require simultaneous attachment of all the antibodies at once. This may limit the amount of markers that may be introduced to the cells due to overlapping of the fluorescent signals. As cells may not be fixed to a certain location in this method, it may not be possible to associate the immunocytochemistry signal of a certain cell to its signal in subsequent downstream detection procedures. A further disadvantage may be that since the cells are not stationary, the time evolution of cellular changes may not be monitored and analyzed.

Microfluidic cell isolation devices may be limited in their application because the high expenses of device operation and each disposable cell cage array and because it may not be possible to trap the cells in cages to limit dilution of the cell lysate.

Electrical and magnetic isolation devices, such as DEP arrays, may not allow analysis of the cell lysate using direct quantitative methods as the solution may be common to all cells in the cell cage array, and diluted by the liquid medium.

Mechanical isolation devices may observe individual cells on microscopic slides, but not manipulate the cells or their environment for cytometric analysis.

An apparatus and method for isolating single cells and performing analysis to each cell individually has been developed. The isolation of the cells may be performed using a suction pump to draw the cells from a liquid medium into a perforated cell cage array, where each cage may be of a size so that only one cell may fit. The perforations of each cell cage may include one large opening, or pore, on the side of the liquid medium with suspended cells to allow one cell to enter each cage, and multiple small openings, or pores, on the side from which the liquid medium is pumped that may be too small for the trapped cell to leave the cage. To trap and isolate the cells a conducting gel lid is positioned adjacent to the cell cage array after the cages are occupied so that all cell cages are closed at once. The analysis may be performed by either recording the reactions of a living cell to various stimulations, or by inducing cell lysis and inspecting each cell's contents. The cell cage is where lysis takes place after cells are captured, and is composed of the cell cage array from the top, and the conducting gel from the bottom. The apparatus may implement an ion-injection technology for introduction of charged molecules to the cells environment without a change in fluid volume. This may be important in the case of lysate analysis since its content is not diluted. This apparatus may not implement costly microfluidic elements, using filters to create a cell cage array.

According to some embodiments of the present invention there are provided methods and apparatuses, for isolation and analysis of individual cells. Using suction, cells suspended in a liquid medium may be drawn into the cages of a cell cage array which may have a large opening, or pore, on the side of the liquid medium with cells, one or more small openings, or pores, on the side of a suction pump, and an enclosure to trap the cell or cells. The cell cages of the array may have cell enclosure dimensions small enough so that only one cell may fit in each cage, the large opening may be large enough for the cell to enter, and the small opening may be too small for the cell to exit the cage. By pumping the liquid medium through the cell cage array, the cells may be drawn into the cages, and then isolated by washing away the liquid medium and pressing the cell cage array against a conducting gel membrane lid.

Once isolated, the cells in the cell cages may be analyzed using cytometric methods adapted to the invention.

Optionally, the apparatus includes a semipermeable membrane, an ion reservoir, a counter electrode electrically connected to the conducting gel, and a working electrode connected to the fluid reservoir, such that an electrical conduction path is established from the conducting gel, through the cell cages of the array, the pumping reservoir, and the semipermeable membrane, and finally to the ion reservoir. By applying an electrical current along this conduction path, ions may be injected into the cell cages and thus used to modify and/or stimulate the cells trapped within the cages. For example, a semipermeable membrane is a bipolar membrane, the ionic fluid is a neutral liquid medium, and a positive current is applied from the conducting gel to the ion reservoir. In this example hydroxyl ions are produced at the bipolar membrane, and drawn by an electrical current into the cell cages to increase the pH of the cell environment. When the pH within the cell cages reaches an approximately value of 11, the cells may undergo lysis and the lysate cell may be analyzed.

Optionally, the cells in the cell cage array are imaged through a window on the bottom of the apparatus. For example, a fluorescent microscope is used to analyze the contents of the cell cage array through the window. For example, a light microscope is used to view the contents of the cell cage array through the window.

As used herein, the term cell cage means a partially or fully enclosed space with dimensions adapted to receive one or more cells. Alternative terms for cell cage may be well, cave, chamber, container, tube, enclosure, depression, pico-well, pico liter well, mini well, nano-well, micro-well, millimeter-scale well, and the like. As used herein, the term cell cage array means a component that has multiple cell cages arranged on a surface of a component. Alternative terms for cell cage array may be well array, cell isolation array, multiwall plate, microwell plate, microwell array, and the like. As used herein, the term opening of a cell cage means a feature of the cell cage that allows fluid and/or cells to pass into and out from the cell cage. Alternative terms for opening may be aperture, pore, window, and the like. For example, a small opening of a cell cage may be an opening that is too small for a cell to pass through, but large enough for a liquid medium to pass through. For example, a large opening of a cell cage may be an opening that is large enough for both cells and liquid to pass through.

Optionally, the cell cage array is detachable from the apparatus. For example, the call cage array is a single-use, disposable cell cage array with between 100 to 1,000,000 cell cages in each array. For example, a cell cage array has 100 cell cages. For example, a cell cage array has 1,000,000 cell cages. For example, a cell cage array has 10,000,000 cell cages. For example, an apparatus is sold without a disposable cell cage array, and the cell cage array can be purchased separately.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, an apparatus, a device, a process and/or a method.

Aspects of the present invention are described herein with reference to flowchart illustrations and/or block diagrams of methods, apparatus, and systems according to embodiments of the invention. It will be understood that each block of the flowchart illustrations and/or block diagrams, and combinations of blocks in the flowchart illustrations and/or block diagrams, can be implemented by computer readable program instructions.

The flowchart and block diagrams in the Figures illustrate the architecture, functionality, and operation of possible implementations of systems, methods, and devices according to various embodiments of the present invention. In this regard, each block in the flowchart or block diagrams may represent a module, segment, or portion of instructions, which comprises one or more actions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 4:
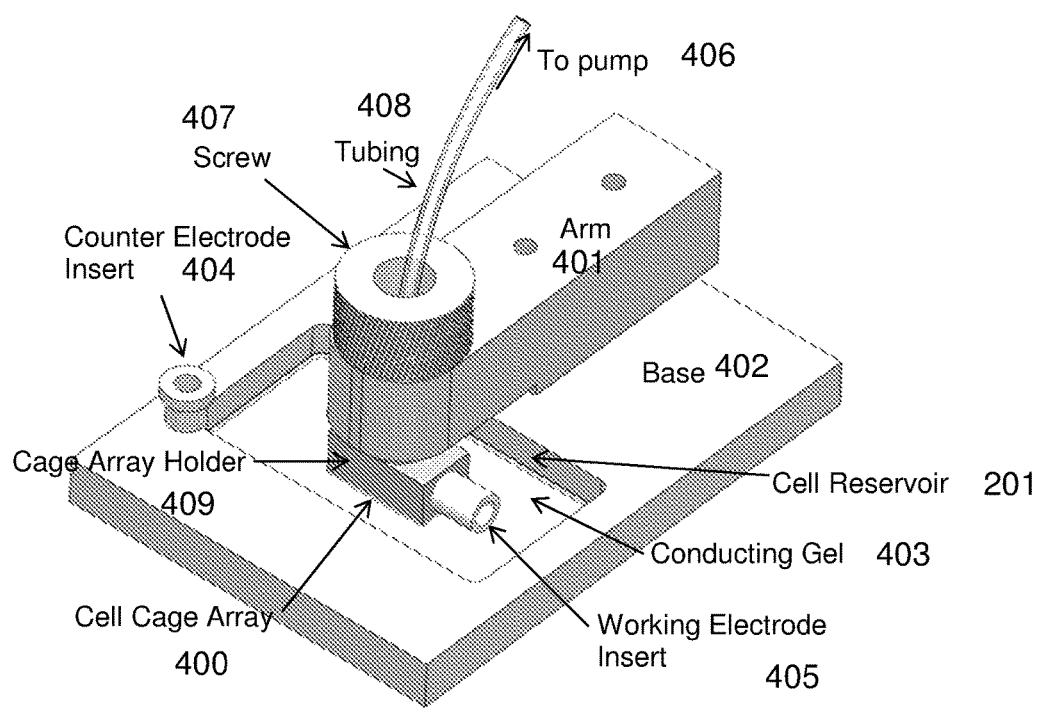
FIG. 4 is a schematic illustration of an apparatus for trapping individual cells and ion injection into the trapped cell surroundings, according to some embodiments of the invention.

Reference is now made to FIG. 4, which is a schematic illustration of an apparatus for trapping individual cells and ion injection into the trapped cell surroundings, according to some embodiments of the invention. The cell cage array 400 may be held in a cage array holder 409 that may be attached to an arm 401. The arm may be used to position the cell cage array in the cell reservoir 201 above the conducting gel 403 that may be located on the cell reservoir floor. The cell reservoir may be located in the base 402 of the apparatus. The enclosed reservoir may be located inside the cage array holder 409, and the suction tubing 408 connects the enclosed reservoir to the suction pump 406. When sufficient cells have occupied the cell cages of the array, a mechanical element may be actuated, in this embodiment a screw 407 may be turned, to press the cell cage large openings against the conducting gel layer 403, such that the gel layer forms a contiguous barrier to the large openings of the cell cages and isolates the cells in each cage.

Optionally, the screw is a lever, linear actuator, or the like.

Optionally, the apparatus is a handheld apparatus and the cell reservoir is not attached to the apparatus. For example, the cell reservoir is a Petri dish containing a liquid medium with suspended cells. The apparatus in this example has a handheld thumb action mechanical pump, such as used in a pipette. Thumb pump button is pressed, the cell array is placed into the liquid medium of the Petri dish, the thumb pump button is released, drawing the cells into the cell array. The cell array is transferred to a second dish containing an isolating gel layer, a second liquid medium, a second cell array, and the like. Depending on the second dish contents and the cell handling protocol, the thumb button may be pressed again to extract the isolated cells, or a second button pressed to disengage the cell array from the apparatus. When the cell cage array is disengaged, such as onto a microscope slide for visual imaging, the isolated calls may be further handled separately from the apparatus for processing, cytometry, analysis, proliferation, and the like.

When ion injection may be required, the working electrode may be connected to the working electrode insert 405, the counter electrode may be connected to the counter electrode insert 404, and current is applied to the electrodes from a current source. The working electrode insert comprises a semipermeable membrane, an ion reservoir, and a female electrical electrode receptacle. The working electrode may be a positive electrode and the counter electrode may be a negative electrode, and vice versa as needed by the ion injection chemistry.

Figure 2A:
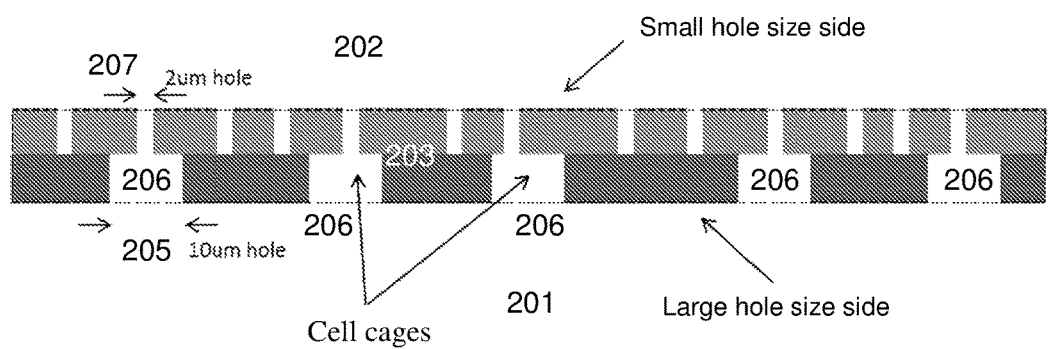
FIG. 2A is a schematic illustration of a cell cage array with cylindrical wells for trapping individual cells, according to some embodiments of the invention.

Reference is now made to FIG. 2A, which is a schematic illustration of a cell cage array with cylindrical wells for trapping individual cells, according to some embodiments of the invention. The cell cage array 203 may contain perforated cell cages 206, with large openings as at 205 for cells to enter each cage on the side adjacent to the cell reservoir 201. Each cage 206 has one or more small openings 207 on the side adjacent to the enclosed reservoir 202. For example, the cell cage array may comprise two polycarbonate membrane filters, bearing 2 micrometer and 10 micrometer holes respectively. Thus, the resulting cell cage array 203 may have holes with 10 μm openings on the side of the cell reservoir 201 and 2 micrometer openings on the side of the enclosed reservoir 202.

For example, commercially available membranes filters are used, such as ISOPORE MEMBRANE FILTERS, catalog numbers TCTP02500 and TCTP02500, manufactured by Millipore, Inc. When such are bonded flat against each other, they may produce the cell cages described herein. For example, a cage array is manufactured by micro-fabrication methods. The cage array may be produced by two negative photoresist layers. A first layer may be a thin layer, approximately 1-5 micrometers thick, of a liquid photoresist containing 1-4 micrometer holes. For example, SU8 2002 manufactured by MicroChem, or SU8 1060 manufactured by Gersteltec Engineering Solutions are photoresist layers used. The second layer may be made of a film photoresist 30 to 100 micrometers thick and containing 100 micrometer holes concentric with the holes of the first layer. For example, a second later photoresist is TMMF S2045 manufactured by Tokyo Ohka Kogyo, or PerMX™ manufactured by DuPont. See the figure attached to the mail. An advantage of a cell cage array manufactured using two photoresist layers is its transparency, enabling the cells within the cages to be observed using bright field microscopy for example, rather than fluorescent microscopy.

Figure 2B:
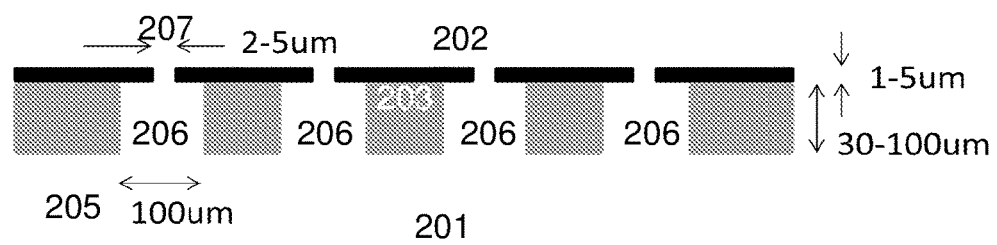
FIG. 2B is a schematic illustration of a cell cage array with cylindrical wells for trapping clusters of cells, according to some embodiments of the invention.

Reference is now made to FIG. 2B, which is a schematic illustration of a cell cage array with cylindrical wells for trapping clusters of cells, according to some embodiments of the invention. As in FIG. 2A, the cell cage array 203 may contain perforated cell cages 206, with large openings as at 205 for cells to enter each cage on the side adjacent to the cell reservoir 201. Each cage 206 has one or more small openings 207 on the side adjacent to the enclosed reservoir 202. Here the dimensions of the cell cages are large enough for two or more cells to occupy each cage, allowing cell clusters to be introduced or cultured in each cell cage of the cell cage array. For example, the cell cage opening and diameter are 100 micrometers. For example, the cell cage depth is between 30 to 100 micrometers. For example, the cell small openings are between 2 to 5 micrometers. For example, the photoresist layer of the small openings is 1 to 5 micrometers thick.

According to some embodiments of the present invention there are provided methods, for cell isolation by pumping a liquid medium with suspended cells through a cell cage array that allow the cells to enter the cage but prevent cells from exiting. Each cage provides a channel for the liquid medium to flow with one large opening on the side of a cell reservoir, and one or more small openings on the side of an enclosed reservoir connected to a suction pump mechanism. The entrance to each cage may be large enough for a single cell to enter each cage, and the size of the cage small enough so that only one cell may fit in each cage. By pumping the liquid medium from the enclosed reservoir, the suspended cells are drawn into the cages, one cell in each cage. When a cell occupies the cage, the cell may block the small openings and thus limit the liquid flowing through that cage and prevent drawing in an additional cell into that cage. Once a sufficient number of cages have been occupied, a flow resistance to the suction may be sensed. This process may be completed by pressing the cell cage array against a conducting gel, which forms a lid over the cell cages.

Reference is now made to FIG. 1, which is a flowchart of a method for trapping individual cells in cages and performing cytometric analysis to each individual cell, according to some embodiments of the invention. A received liquid medium with suspended cells 101 may be placed in a cell reservoir 102 fitted with a cell cage array. The pump may be activated to draw the liquid medium from the enclosed reservoir 103 until sufficient cell cages have been occupied 104. The conducting gel layer may be moved 105 adjacent to the large opening side of the cell cage array to trap the cells in their respective cages. When ion injection is required as at 106, the working electrode insert is prepared by attaching a membrane with glue 109 to the working electrode and filling the ion reservoir 110 with the ionic fluid. The working and counter electrodes are connected 109, and an electrical current may be applied 112. When ion injection is not required or has the ion injection has completed, the cytometric analysis may be performed 107 and the results of the analysis outputted 108 to the user.

In the present apparatus and method, the cells may be at a fixed location throughout the detection procedure. This enables performing multiple immunochemistry experiments serially and so overcomes the limitation of signal overlapping found in flow cytometry. The cell cage may also enable performing subsequent detection procedures such as lysate analysis with direct quantification as the contents of the cell cage may not be diluted.

Since each cell may be captured in its own cage, individual immunochemical analysis of each cell may be performed. Furthermore, this process may be done serially with multiple antibodies.

Figure 6:
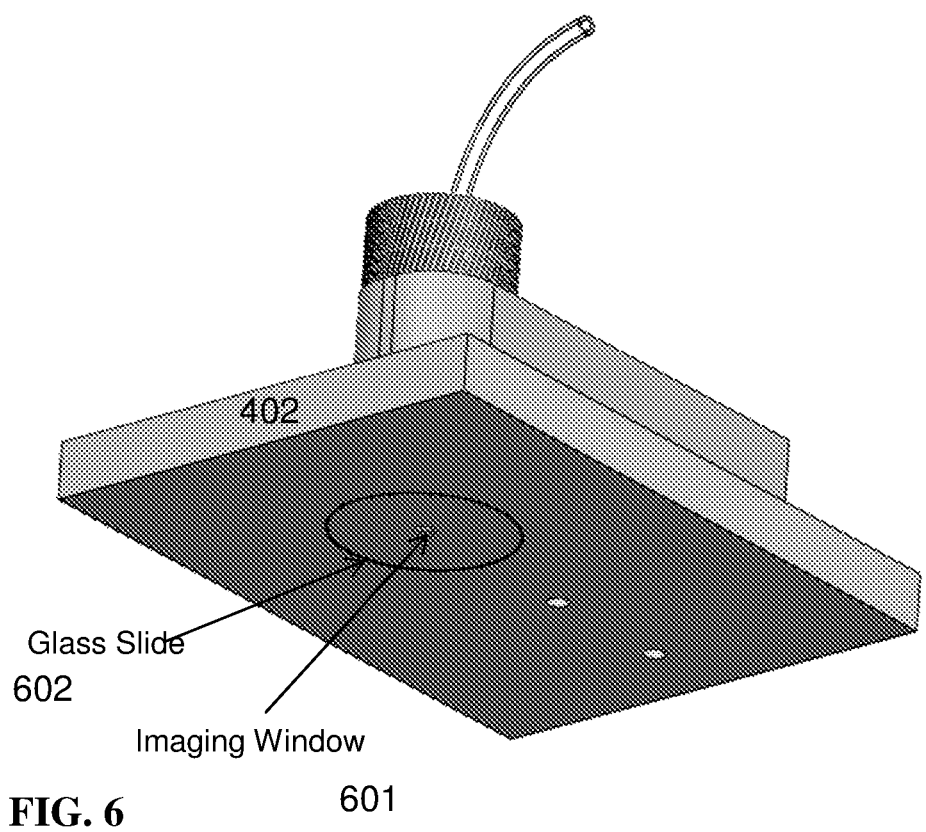
FIG. 6 is a schematic illustration of the bottom side of an apparatus for trapping individual cells, according to some embodiments of the invention.
Figure 7:
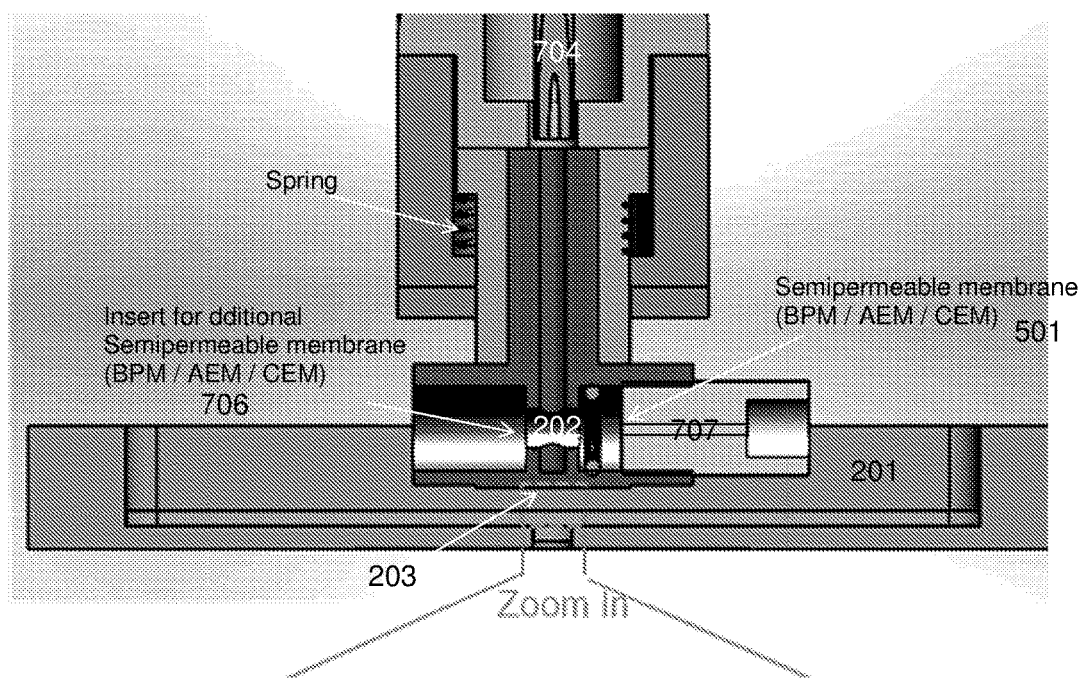
FIG. 7 is a cross sectional schematic illustration of an apparatus for trapping individual cells, according to some embodiments of the invention.

The cell isolation procedure may be described by two stages—an assembly stage and a capture stage. The assembly stage comprises attaching a glass slide and/or other transparent support to its position on the base window. Reference is now made to FIG. 6, which is a schematic illustration of the bottom side of an apparatus for trapping individual cells, according to some embodiments of the invention. The apparatus base 402 may have an imaging window 601 covered by a transparent support 602.

Reference is now made, once again, to FIG. 4. A conducting gel 403 may be poured into the base 402, typically about 2 to 3 milliliters. A spring is inserted in an arm, the cell cage array 400 into the cage array holder 409, and the screw 407 to the position on the arm 401. Tubing 408 to a suction pump 406 may be connected to the cell cage array holder 409, and the holder connected to the arm 401. The counter electrode insert 404 may be placed in its position in the base 402, and the arm 401 may be attached to the base 402. The suction tubing 408 may be connected to the suction pump 406.

Figure 5:
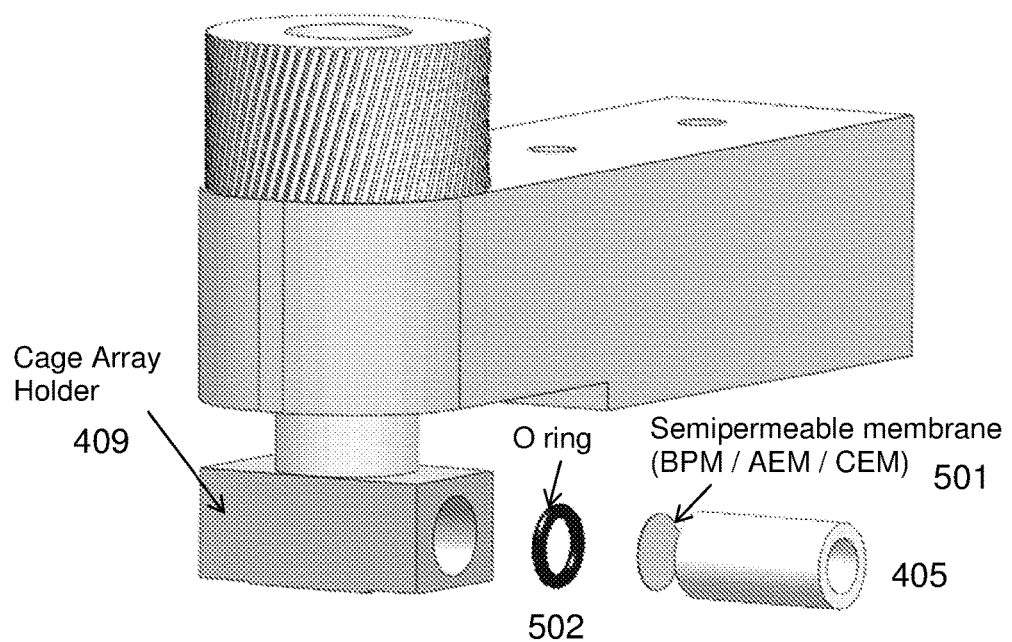
FIG. 5 is a schematic illustration of the details of an apparatus for trapping individual cells and ion injection into the trapped cell surroundings, according to some embodiments of the invention.

Reference is now made to FIG. 5, which is a schematic illustration of the details of an apparatus for trapping individual cells and ion injection into the trapped cell surroundings, according to some embodiments of the invention. When ion injection may be required, a semipermeable membrane 501 may be glued to the working electrode insert 405, and the working electrode insert may be filled with the appropriate ionic fluid. For example, when hydroxide ions are to be injected, the insert may be filled with 150 millimolar NaCl solution. The working electrode insert may be screwed to its position in the cage array holder 409 with an o-ring 502 to make a liquid tight seal. A semipermeable membrane may be attached to the counter electrode insert, and filled with 150 mM NaCl solution. For example, when hydroxyl ions are to be injected than the semipermeable membrane to attach may be anion exchange membrane.

Figure 8:
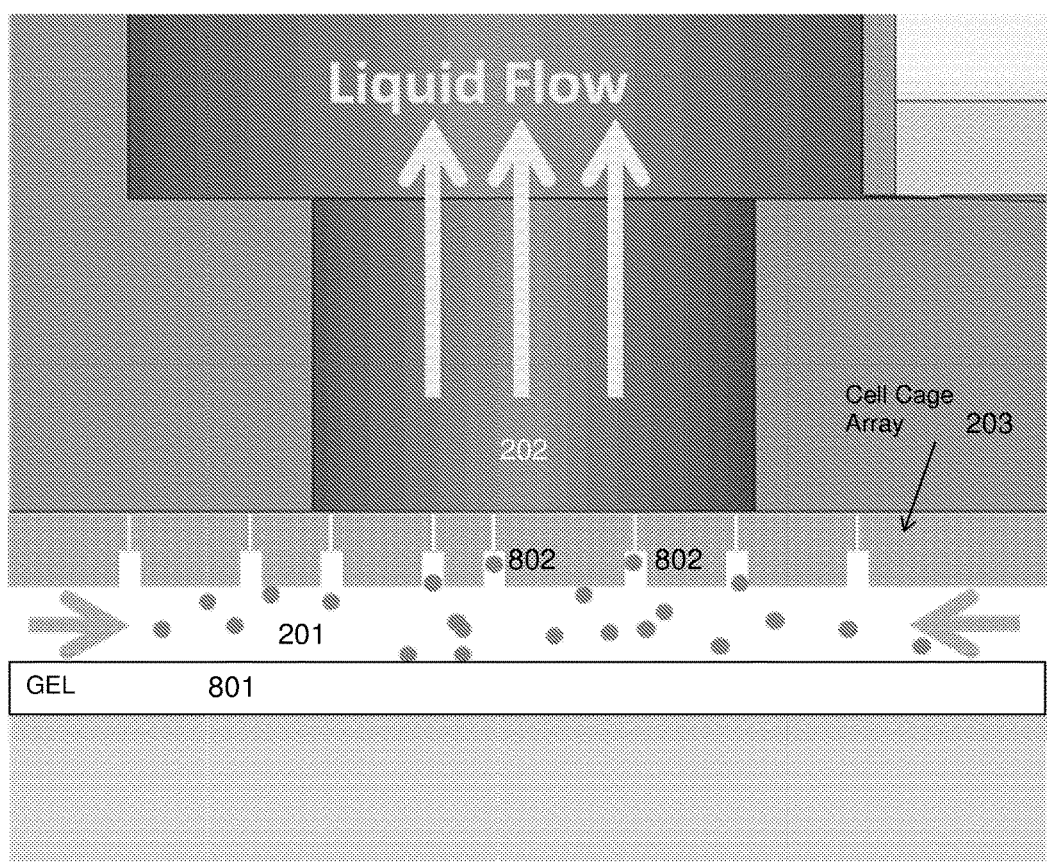
FIG. 8 is a detailed cross sectional schematic illustration of an apparatus for trapping individual cells shown during cell capture, according to some embodiments of the invention.
Figure 9:
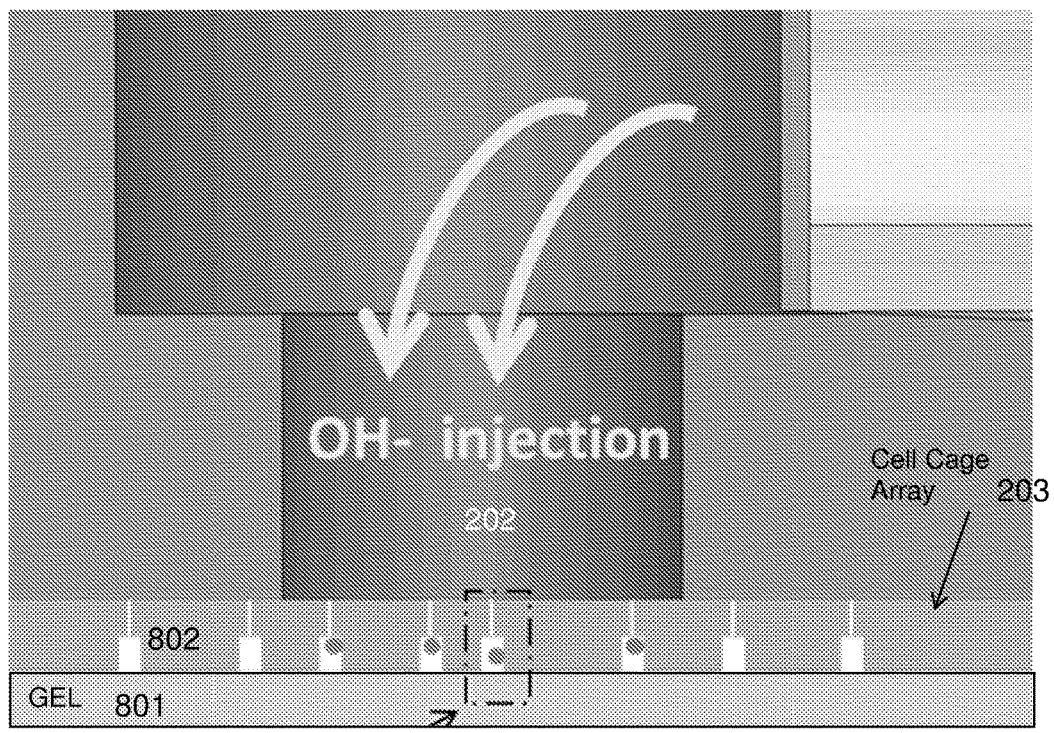
FIG. 9 is a detailed cross sectional schematic illustration of an apparatus for trapping individual cells shown during ion injection, according to some embodiments of the invention.

During the cell capture stage the screw may be turned to lift the cell cage array to at least 2 millimeters above the conducting gel. About 1 milliliter of the liquid medium with suspended cells may be placed in the cell reservoir. Reference is now made to FIG. 8, which is a detailed cross sectional schematic illustration of an apparatus for trapping individual cells shown during cell capture, according to some embodiments of the invention. Liquid medium 201 may be pumped from the enclosed reservoir 202 and cells 802 accumulate in the cell cage array 203 until the array has sufficient cells for analysis. Reference is now made to FIG. 9, which is a detailed cross sectional schematic illustration of an apparatus for trapping individual cells shown during ion injection, according to some embodiments of the invention. The cell cage array 203 may be lowered by turning the screw until the cell cage array gently presses against the conducting gel 801 completing the cell capture. This forms an ion conduction path for ion injection from the working electrode insert electrically connected to the enclosed reservoir 202, through the cell cages 206, through the conducting gel 801, and to the counter electrode electrically connected to the conducting gel.

Optionally, the cell capture process is self-limiting, ensuring that no more than a single cell is to be captured in each cage. This may be because captured cells block the small openings in their cage, thereby diminishing the force drawing additional cells into that cage.

Figure 16:
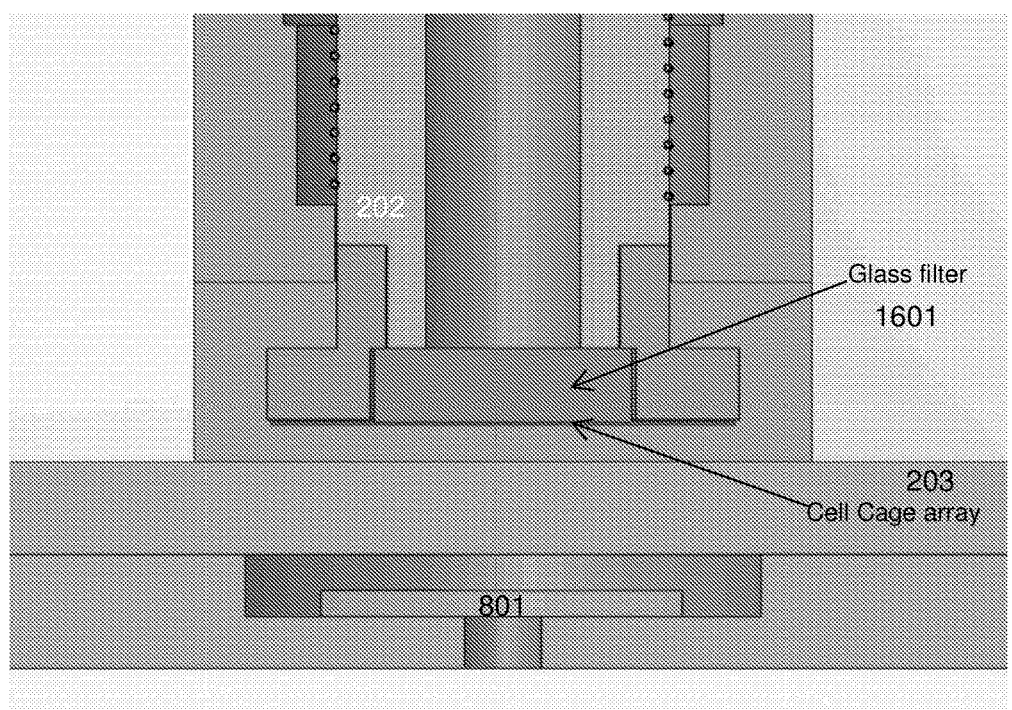
FIG. 16 is a detailed cross sectional schematic illustration of an apparatus for trapping individual cells showing a filter backing for cell cage array, according to some embodiments of the invention.

Optionally, the cell cage array has a support structure, such as a glass filter and or the like, as a rigid backing between the cell cage array and the enclosed reservoir. Pressing the cell cage array, using the support structure, against the conducting gel may isolate all the individual cells in the cell cages without the cell cage array changing shape by the pressure against the conducting gel. Reference is now made to FIG. 16, which is a detailed cross sectional schematic illustration of an apparatus for trapping individual cells showing a support structure backing for cell cage array, according to some embodiments of the invention. For example, a glass, Polyethylene, and the like support filter 1601 may be placed between the cell cage array 203 and the enclosed reservoir 202 so that the cell cage array remains flat while being pressed against the conducting gel 801. For example, a Sintered Glass Filter catalog number 251510406 is used, manufactured by DURAN Group GmbH. For example, a polyethylene filter catalog number POR-4898 is used, manufactured by Interstate Specialty Products, Inc.

Perturbing the cell's environment may be done by modifying the pH and salt environment of the cages using electrical ion injection. Electrical ion injection may be performed by semipermeable membranes, ionic fluid and an electrical conducting path through the cell cages. Larger charged molecules such may also be introduced through ion exchange membranes. Still larger molecules or neutral ones, may be introduced by transferring the cell cage array with the cells to new solutions containing these larger molecules.

Optionally, there is no limitation regarding the salt profile of the liquid medium.

Optionally, for cell lysis, non-buffered solutions are preferable as they shorten the time to reach the pH level necessary for lysis.

After the cells have been trapped in the cages by the conducting gel lid, the procedure for ion injection continues with removal of excess solution from the cell reservoir. The cells may be lysed by modifying their pH and/or salt environment. The following is an example of how to do so by injecting hydroxyl ions. Optionally, cell lysis may be achieved by salt depletion, sodium dodecyl sulfate (SDS) injection, and the like.

Figure 10:
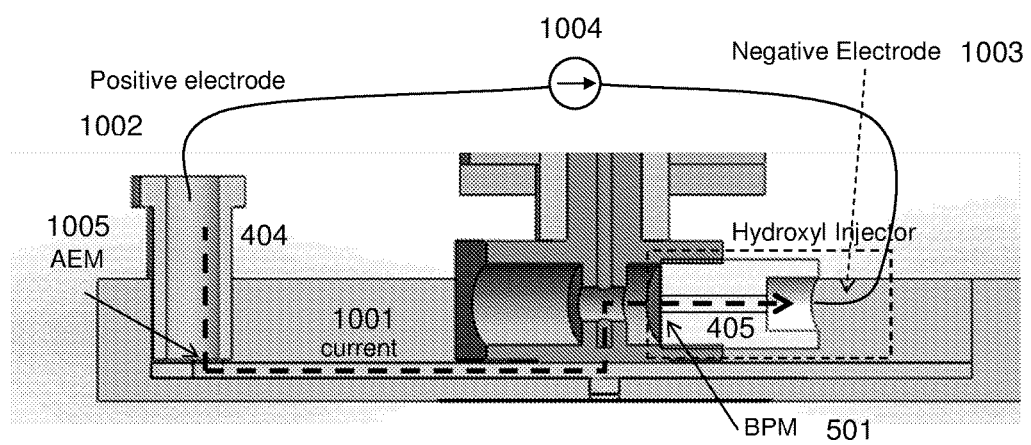
FIG. 10 is a cross sectional schematic illustration of an apparatus for trapping individual cells shown during ion injection, according to some embodiments of the invention.

Optionally, hydroxyl ions are produced and injected into the cell cages using a bipolar membrane. Reference is now made to FIG. 10, which is a cross sectional schematic illustration of an apparatus for trapping individual cells shown during ion injection, according to some embodiments of the invention. Positive current 1001 may be applied from a positive electrode 1002 positioned in the counter electrode insert 404, to a negative electrode 1003 positioned in the working electrode insert 405. In this option, the current induces hydroxyl ion production at the bipolar membrane 501 (BPM). Reference is now made, once again, to FIG. 9. These anions migrate electrically towards the positive electrode 1002 through the enclosed reservoir 202 and cell cage 206, raising the cell cage pH and inducing cell lysis. Current may be applied through a current source 1004 connected to the working and counter electrode inserts. An anion exchange membrane 1005 (AEM) may be placed in front of the counter electrode to prevent entrance of cations into the gel. Hydroxyl ion injection may be activated by applying 2 milliampere current between the counter electrode and the working electrode. The counter electrode may have the positive voltage. Cells undergo lysis once the pH level in the cell cages reaches a value of approximately 11.

Optionally, a conductive gel layer is attached to the cell cage array on its small opening side, adjacent to the enclosed reservoir side, to prevent outward diffusion of the lysate components.

Figure 11:
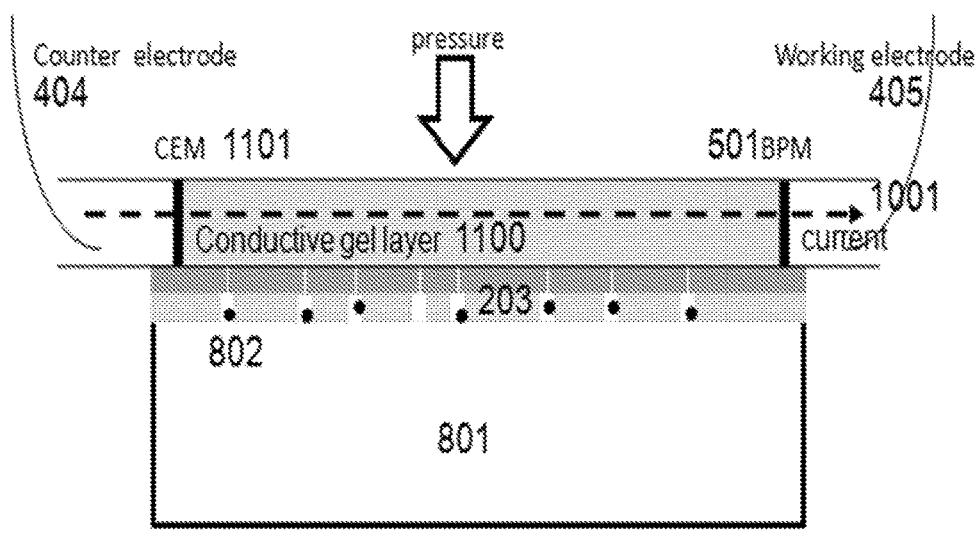
FIG. 11 is a detailed cross sectional schematic illustration of an apparatus shown during ion injection by diffusion, according to some embodiments of the invention.

Optionally, a conductive gel layer is attached to the cell cage array on its small opening side, adjacent to the enclosed reservoir side, to allow ion injection by diffusion. Reference is now made to FIG. 11, which is a detailed cross sectional schematic illustration of an apparatus for ion injection by diffusion, according to some embodiments of the invention. Here, a diffusing gel layer 1100 may be placed above the cell cage array 203, adjacent to the small opening side. The gel may be pressed against the cell cage array 203 to ensure good contact to the cell cages. Once current 1001 may be applied between the working 405 and counter 404 electrode inserts, hydroxyl ions may be produced in the bipolar membrane 501, and injected to the gel 1100. Hydroxyl ions that accumulate inside the gel 1100 penetrate the cell cages by diffusion and reach the cells 802. The diffusion process may not take a long time since the distance from the gel to the cell cage may be very short. In this way, any type of salt may be introduced to the cage. Optionally, the conductive gel layer 1100 functions as an adsorbing layer. The counter electrode insert 404 may have a cation exchange membrane 1101 (CEM) attached. Having no electric field present inside the cell cage may be beneficial in certain cases.

Optionally, substances may be introduced into the array without applying a current and or flow through the cell cage. For example, a gel is preloaded with the necessary substances, and pressed against the cell array. The substances then diffuse from the gel into the cell cages. The loading of the substances into the gel may be done by casting the gel with a solution containing these substances. For example, the substances could be detergents, enzymes, nutrients, and the like.

Optionally, to prevent outerward diffusion of the lysate components from the large opening side of the cell cage array, a cutoff membrane, such as dialysis membrane, may be placed between the conducting gel and the cell cage array. A cutoff membrane may be a porous membrane with molecule-scale pore size. This membrane prevents molecules larger than the pores from going through the membranes. For example Standard RC Dialysis Tubing, 1 kD, catalog number: 132636 manufactured by Spectrum Laboratories, Inc.

Optionally, a chemical and/or material is introduced into the cell cages by diffusion using introduction of a liquid containing the chemical and/or material into the enclosed reservoir. For example, lithium atoms are introduced into the cell cages by direct pipetting of a liquid containing the atoms into the enclosed reservoir after the individual cells have been isolated and in this case the electrodes are not necessary.

Optionally, cytometric analysis may include any of the actions of culturing, applying stimuli, immunocytochemical analysis, western blot, gel electrophoresis, protein purification, green fluorescent protein, protein immunostaining, protein sequencing, protein electrophoresis, protein immunoprecipitation, peptide mass fingerprinting, dual polarization interferometry, microscale thermophoresis, chromatin immunoprecipitation, surface plasmon resonance, nucleic acid analysis, optical analysis, protein analysis, fluorescent image analysis, cytophotometry, electroporation, genomics, transcriptomics, proteomics, metabolomics, spectrophotometery, and/or the like.

Optionally, after the cell is lysed, the cell lysate is transferred to a substrate for further analysis. The following may be possible ways to implement the analysis of proteins.

Optionally, electric field is applied for transferring the lysate across the gel to an adsorbing layer, such as a nitrocellulose membrane. As the pH inside the cell cages may be high, most of the lysate ingredients may be negatively charged. A positive voltage at the counter electrode may direct the negatively charged lysate contents towards the adsorbing layer.

Figure 12:
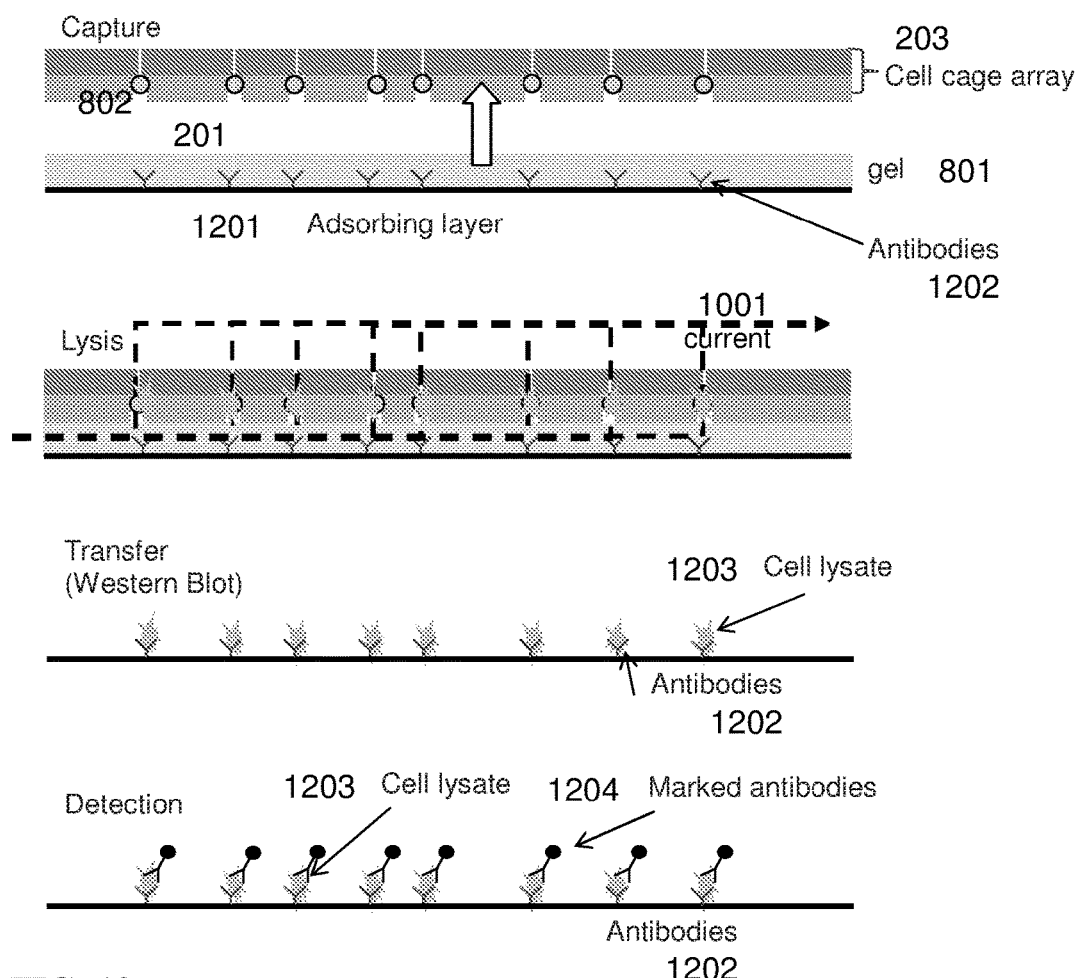
FIG. 12 is a detailed cross sectional schematic illustration of an apparatus for trapping individual cells, ion injection, and cytometric analysis, according to some embodiments of the invention.

Reference is now made to FIG. 12, which is a detailed cross sectional schematic illustration of an apparatus for trapping individual cells, ion injection, and cytometric analysis, according to some embodiments of the invention. Following cell lysis, the cell cage array 203 may be pressed against a gel lid 801 with an adjacent adsorbing layer 1201. An electric current 1001 may be applied, directing the cell lysate 1203 across the conducting gel to the adsorbing layer. When a certain component of the cell lysate 1203 may be desired, the layer may be modified with antibodies 1202 to bind this component. Otherwise all lysate components may attach to the adsorbing layer. Optionally, detection of one lysate component or more may be performed using standard immunochemical detection methods, for example with marked antibodies 1204.

Optionally, the lysate components are transferred to the conducting gel by applying an electrical field. Since the diffusion coefficient in the gel may be significantly low, the latter may store the lysate for extended periods of time. The conducting gel may be transferred and analyzed at a later time.

Figure 13:
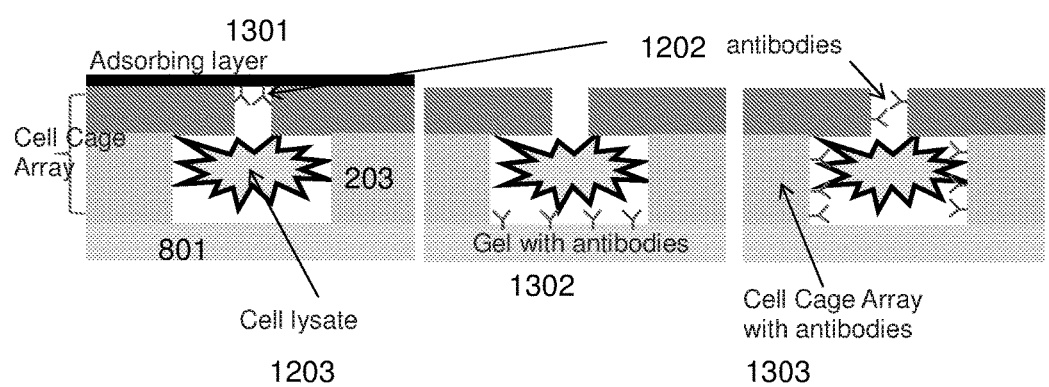
FIG. 13 is a detailed cross sectional schematic illustration of an apparatus for immunocytochemical analysis of the lysate from an individual cell, according to some embodiments of the invention.

Optionally, the lysate is adsorbed to an adsorbing layer with no electric field applied. Reference is now made to FIG. 13, which is a detailed cross sectional schematic illustration an apparatus for immunocytochemical analysis of the lysate from an individual cell, according to some embodiments of the invention. Adsorption may take place by attaching an adsorbing layer 1301 to the upper side of the cell cage array, adjacent to the small opening side of cell cage array 203. When a certain component of the lysate 1203 may be desired the layer may be modified with antibodies 1202 to bind this component. After an appropriate incubation time, detection may be performed using standard immunochemical detection methods.

Optionally, the conducting gel 1302 and/or the cell cage walls 1303 may perform as adsorbing layers, by modifying their surface with antibodies 1202 to bind one or more of the lysate 1203 components.

Optionally, to enhance antigen-antibody binding, salt and pH levels inside the cell cages may be modified to values favoring such interaction as soon as cell lysis is completed. For example, the cell is lysed by raising the pH to 11, and phosphate ions ($H2PO4-$) are injected through an anion exchange membrane (AEM) to reduce the pH levels inside the cell cage.

Optionally, similar methods may be performed to isolate messenger ribonucleic acid (mRNA) from the lysate. For example, a Poly-T single stranded deoxyribonucleic acid (DNA) contains repetitive thymine nucleobase molecules and captures a messenger ribonucleic acid molecule (mRNA) which has a complimentary repetitive adenine (Poly-A) tail. When a cell expresses a certain protein, the cell may create a copy of the DNA encoding for that protein. This copy is referred to as the mRNA molecule corresponding to that protein. It contains a copy of the DNA sequence and a Poly-A tail. The mRNA may attach to the ribosome which than produces the protein according to the mRNA sequence. Since all mRNA may have a Poly-A sequence, they may be captured efficiently using a Poly-T DNA sequence. Thus an antibody may bind the whole mRNA population using a Poly-T DNA tail. Transforming the captured mRNA to complementary deoxyribonucleic acid (cDNA) and polymerase chain reaction (PCR) amplification may be implemented inside the cages, enabling single cell transcriptomics. PCR process may be feasible due to the easy manipulation of the cell temperature, for example, by attaching the cell cage array to an electrically controlled heat source.

Optionally, electroporation is performed on the isolated cells in the cell cage array, enabling DNA to be inserted to the cells and/or bacteria. This procedure may cause the cell and/or bacteria express a certain gene which may not be included in the original genome. The DNA molecule may contain at least two elements, the gene that the cell and/or bacteria may express, and a reporter gene which may help discover when the cell contains the DNA molecule. For example, the reporter gene encodes for a fluorescent protein. First, DNA may be inserted to a solution containing the cells and/or bacteria. Subsequently, a strong electric field may be applied to the cell and/or bacteria causing them to undergo temporal perforation. During this process, the DNA molecules may enter a certain percentage of the cells and/or bacteria perforations. Subsequently, the voltage may be turned off and the cells may be allowed to recover. After a few hours, the cells that survived the electric field and contain the DNA may express the fluorescent protein. Through fluorescent imaging one can detect which cells were electroporated successfully.

Optionally, electroporation may be implemented in individual single cells. The DNA may be inserted to the cell cages after the cells are captured and isolated. This may be done electrically, by diffusion, and the like. The electric field may be applied using the working and counter electrodes. The fluorescence detection may be done through the imaging window.

Optionally, an apparatus may be used for immunocytochemical analysis. In this detection technique, cells may be introduced to antibodies to bind various antigens present on the membrane of the cell. Detection of such antigens may be important to classify the cells. The apparatus may be capable of performing such experiments to each cell individually, enabling detailed analysis of antigens in large cell populations. For example, a procedure of single cell immunocytochemistry may be performed by capturing the cells in the cell cage array. The cell cage array may be transferred to and incubated in a solution containing antibodies to bind one of the cell's antigens. The cell cage array may be transferred to and incubated in a washing solution, to remove non-specifically bound antibodies. A detection reaction may be performed, for example with a secondary marked antibody, to detect the presence of the primary antibodies.

Optionally, cells may be cultured for extended periods of time by preconditioning the cell cage solution with the necessary ingredients for cell maintenance. Optionally, cells also proliferate.

Optionally, cell analysis monitors the cell response to various stimulations while keeping the cell alive. For example, T cells of the immune system are activated by introduction of antibodies against their CD28 receptor. Upon activation, these cells may secrete cytokines such as IL-2 and INFγ. The ability to stimulate cells and inspect their individual response may be important for research purposes, such as identifying new cell subpopulations, as well as for clinical ones, such as investigating cell response to drugs.

Optionally, stimulations such as pH and salt modifications may be performed by implementing the ion and pH injectors. Optionally, larger charged molecules, such as serotonin, may also be introduced by implementing the ion and pH injectors.

Figure 14:
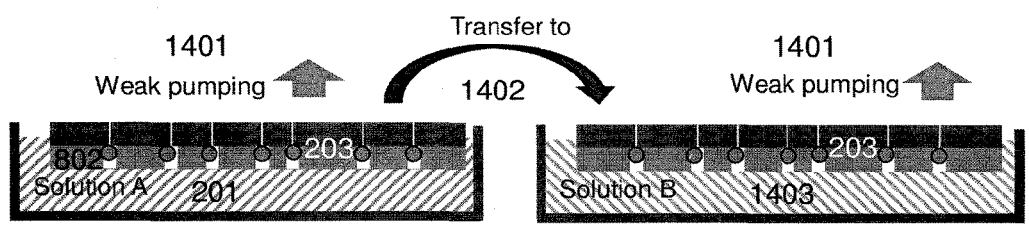
FIG. 14 is a cross sectional schematic illustration of an apparatus for transfer of cell cage array to a new solution, according to some embodiments of the invention.

Optionally, still larger molecules, such as cytokines, or neutral ones, such as glucose, may be introduced by transferring the cell cage array from one solution to another. For example, single cells may be treated with various components by introducing them to preconditioned solutions. Reference is now made to FIG. 14, which is a cross sectional schematic illustration of an apparatus for transfer of cell cage array to a new solution, according to some embodiments of the invention. Subsequent to the cell cage array having sufficient cells, weak pumping 1401 may be performed prior to closing the cell cage array with the conducting gel. The pump may be operated to produce weak pumping during this process to prevent cells 802 from escaping the cages of the array 203. When weak pumping 1401 may be active, the cell cage array 203 may be transferred 1402 from the liquid medium solution 201 to a different liquid medium 1403. To analyze cell secretion in response to stimulations, the cell cage array may be pressed against some adsorbing layer which adsorbs the secreted material. Detection of adsorbed material may be performed as described above. Intracellular responses may be detected by inducing cell lysis and inspecting the resulting lysate components.

Optionally, the orientation of the apparatus is reversed, so that the cell cage array is on the base of the apparatus, the pump is connected to an internal channel in the base, and the conducting gel is connected to the arm. For example, the reversed orientation apparatus allows the use of gravity to further draw the cells into the cell cages.

Optionally, the mechanical element that moves the cell cage array adjoining the conducting gel layer is any from the list of screw, lever, linear actuator, worm drive, step motor, and the like. For example the screw is turned causing the cage array holder to move in the direction of the conducting gel layer until the large openings of the cell cage array are blocked by the gel layer.

Optionally, the mechanical element is motorized.

Optionally, the motorized mechanical element is controlled by an electric controller and/or computer.

Optionally, the apparatus further comprises a gel layer application device that manually and/or automatically prepares a conducting gel layer. For example, the gel layer device comprises a gel reservoir and a spigot, and when a gel layer is needed, the spigot is opened to allow the required amount of gel to enter the cell reservoir and harden to a conducting gel layer.

Figure 3:
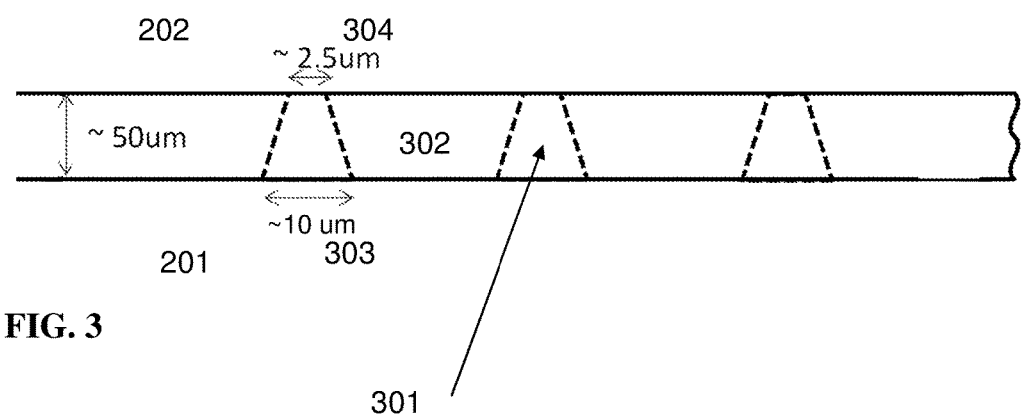
FIG. 3 is a schematic illustration of a cell cage array with conical wells for trapping individual cells, according to some embodiments of the invention.

Optionally, this cell cage array is composed of a thin poly-methyl methacrylate membrane perforated with conical wells. Reference is now made to FIG. 3, which is a schematic illustration of a cell cage array with conical wells for trapping individual cells, according to some embodiments of the invention. The opening dimensions of the wells 301 may be similar to those of the two layer cell cage array. On the side of the array adjacent to the cell reservoir 201, the opening dimension 303 may be slightly larger than the cell size. For example, the opening dimension on the cell reservoir side may be approximately 10 micrometers. On the side of the array adjacent to the enclosed reservoir 202, the opening dimension 304 may be smaller than the cell size. For example, the opening dimension on the enclosed reservoir side may be approximately 2.5 micrometers. Optionally, a variety of cage sizes may be produced to fit the different cell types.

Analyzing the cell lysate, when lysis may be induced, or the cell secreted proteins may be performed by immobilization of the lysate and/or proteins to some adsorbing layer. Optionally, transfer of the cell lysate to the adsorbing layer is achieved by using an electric field to direct the charged components. Optionally, transfer of the cell lysate to the adsorbing layer is achieved by placing the layer in close proximity to the cell cage and incubating to allow adsorption.

Optionally, the absorbing layer has a high capacity to adsorb bio-molecules. For example, nitrocellulose, polyvinylidene difluoride (PVDF) and low fluorescence PVDF layers. This layer adsorbs lysate bio-molecules that may be later detected using conventional methods such as immunochemical detection.

Optionally, the suction pump draws liquid through the cell cage array for cell isolation. Optionally, the suction pump is composed of a simple 1 milliliter syringe whose piston is accurately manipulated with a micrometer. Optionally, the pump is composed of electrical liquid pump and monitored using computerized digital controls. Optionally, the suction pump is composed of computerized automatic syringe. Optionally, the suction pump is any from the list of an electrical pump, a micropump, a manual syringe with attached caliper, an automatic programmable syringe, a computerized syringe, a syringe driver, a syringe pump, a programmable syringe pump, a media dispenser, an inductive pump, a pressure injection cell dispenser, an infusion pump, a peristaltic pump, and the like.

Optionally, the suction pump is operated by a controller and/or computerized controller. For example, the suction pump is controlled by a computer comprising a processing unit and a flow sensor. The computerized controller may have a feedback loop using the flow sensor to control a constant flow rate. When the controller has to increase the suction pump effort above a threshold that indicates sufficient cells have entered cell cages, the controller changes to a lower pump rate to hold the cells in the cages. This lower pump rate is continued until a conducting gel layer is moved adjoining the cell cage array on the side of the large openings so that a contiguous barrier is formed to trap each cell in each cell cage.

Optionally, the suction pump liquid exhaust is received by the cell reservoir so that the liquid medium is not depleted when the number of suspended cells is low.

Optionally, a second ion reservoir and second working electrode insert is placed parallel to the first working electrode insert, so that ion injection is performed by diffusion between the two working electrode inserts.

Optionally, the second ion reservoir is used to allow greater ion flux through the cell cage array to the counter electrode insert.

Optionally, the second ion reservoir is used for injection of an additional chemical and/or material not present in the first ion reservoir.

Optionally, the cells are fluorescently and/or optically visualized through the imaging window.

Optionally, the imaging window comprises and incorporated imaging device. For example, the imaging window contains a microscopic imaging camera.

Optionally, the incorporated imaging device is a computerized imaging device.

Optionally, the incorporated imaging device can be used to monitor the number of cells occupying cell cages.

Optionally, the conducting gel functions as a current carrier when one or more of the injectors are in operation. Optionally, the conducting gel functions as a transparent cell cage lid through which the cells are visualized. Optionally, the conducting gel is composed of agarose dissolved in an aqueous solution, acrylamide, bisacrylamide mixtures, and/or the like.

Optionally, the semipermeable membrane is any from the list of a cation exchange membrane (CEM), a charge mosaic membrane (CMM), a bipolar membrane (BPM), an anion exchange membrane (AEM), an alkali anion exchange membrane (AAEM), and a proton exchange membrane (PEM).

Optionally, the o-ring seal comprises an integrated semipermeable membrane, so that the semipermeable membrane is not glued to the working insert. Optionally, the o-ring seal is a gasket. Optionally, the semipermeable membrane is an insert in the o-ring seal so that the o-ring seal is reused but a new membrane is inserted for each operation of the apparatus.

Optionally, the ion injector controls the pH level in the cell's environment by injecting either proton or hydroxide ions into the cell cages. These ions may be generated by applying an appropriate current through a bipolar membrane (BPM).

Optionally, the ion injector controls the salt profile in the cell's environment. This profile may be generated by injection and extraction of salt ions, such as Na+, Cl−, HPO4−2, into the cell cage. For example, ions are injected by applying an appropriate current through the cation exchange membrane (CEM) and the anion exchange membrane (AEM). Optionally, larger charged molecules, such as SDS and small proteins, may also be injected or removed using the ion injector.

Optionally, the apparatus is a computerized apparatus further comprising any of a computerized controller, a processing unit, an interface to the mechanical element controller, an interface to the suction pump controller, and a user interface. For example, the computerized apparatus receives a command to initiate the capture stage, operates the suction pump to draw the suspended cells into the cell cage array. When a flow rate is detected below a threshold indicating sufficient cells been drawn into the cell cages, the pump rate is lowered to maintain the cell positions in their respective cages. The computerized controller indicates to the operator that the mechanical element should be operated to trap and isolate the cells in the cell cages.

Optionally, the computerized controller and/or processing unit send a command to a controller of a motorized mechanical element to adjoin the cell cage array with the conducting gel layer and trap the isolated cells in the cell cages.

Optionally, the user interface is a panel of indicators and buttons. Optionally, the user interface is a computer screen, keyboard, and computer mouse. Optionally, the user interface is a computerized touch screen.

Optionally, the processing unit is an embedded microcontroller configured to operate the apparatus.

Figure 15:
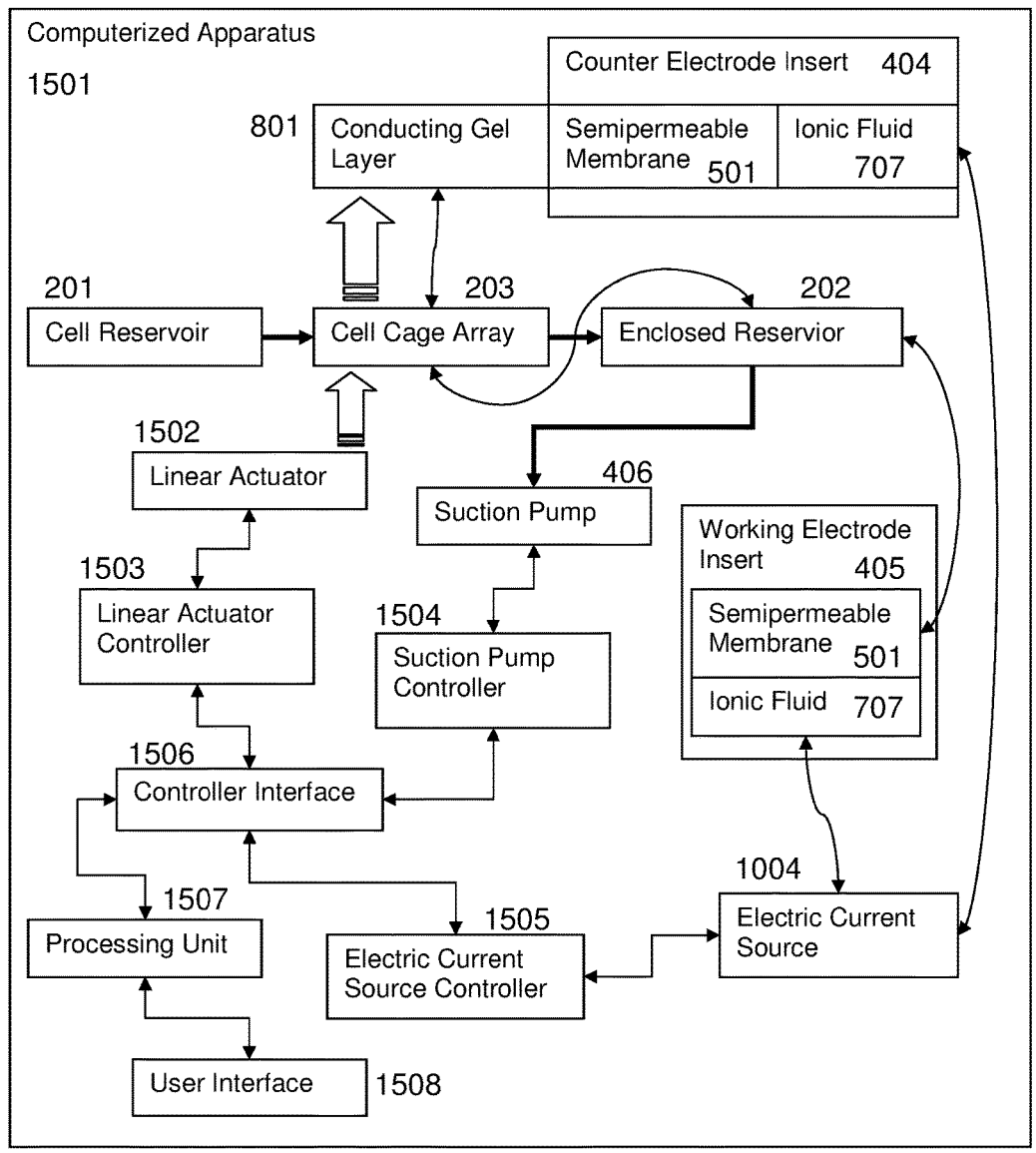
FIG. 15 is a schematic illustration of a computerized apparatus for trapping individual cells in cages and performing cytometric analysis to each individual cell, according to some embodiments of the invention.

Reference is now made to FIG. 15, which is a schematic illustration of a computerized apparatus for trapping individual cells in cages and performing cytometric analysis to each individual cell, according to some embodiments of the invention. The computerized apparatus 1501 may comprise one or more processing units 1507, one or more user interfaces 1508, and one or more controller interfaces 1506. Based on the commands received from the user through the user interface 1508, the processing unit 1507 may control the other components using the controller interface 1506. The controller interface 1506 may send commands and receive statuses from the electrical current source controller 1505, the suction pump controller 1504, and the linear actuator controller 1502. For example, when the suction pump controller 1504 receives the command to begin pumping the liquid medium from the enclosed reservoir 202, the suction pump 406 is activated. The bold arrows may show the path of liquid medium transfer from the cell reservoir 201, through the cell cage array 203, into the enclosed reservoir 202 and from there to the suction pump 406. When sufficient cells have entered the cell cages, the processing unit 1507 may send a command to the linear actuator controller 1503 to activate the linear actuator 1502 and the cell cage array may be pressed against the conducting gel layer 801 to trap the isolated cells.

To inject ions into the cell cages, the processing unit 1507 may send a command to the electric current source controller 1505 and the electric current source 1004 may be activated. The electric current source 1004 may generate an electrical current from the working electrode insert 405, through the enclosed reservoir 202, the cell cage array 203, the conducting gel layer 801, to the counter electrode insert 404 and back to the electric current source 1004 to close the current loop. The current flow loop may be shown by the curved arrows. The current through the working electrode insert 405 may flow through the ionic fluid 707 and semipermeable membrane 501 to release ions into the enclosed reservoir. For example, the current through the working electrode insert 405 flows through the ionic fluid 707 and semipermeable membrane 501 to release anions into the enclosed reservoir 202 and from there to the cells in the cell cage array 203. For example, the current through the counter electrode insert 404 flows through the ionic fluid 707 and semipermeable membrane 501 to release cations into the enclosed conducting gel layer 801 and from there to the cells in the cell cage array 203.

Optionally, when cells are captured and isolated inside the cages, conditions are set to enhance their culture and proliferation. Proliferation may produce a sub-clone containing multiple identical daughter cells carrying similar genomic and epigenetic information. Culturing and proliferating single cells is important when it is desirable to perform multiple tests on identical cells. For example, genomic analysis carried out together with transcriptomics may render a deeper understanding of the cell's identity and state. However, such tests performed on a single cell may require the challenging task of sorting the cell's content. In other cases, it may be necessary to perform multiple tests on living cells, for example, monitoring their response to different types of drugs. In the examples described herein, single cell culturing facilitates these procedures by producing multiple copies of the same identical cell where each is treated differently.

Figure 17A:
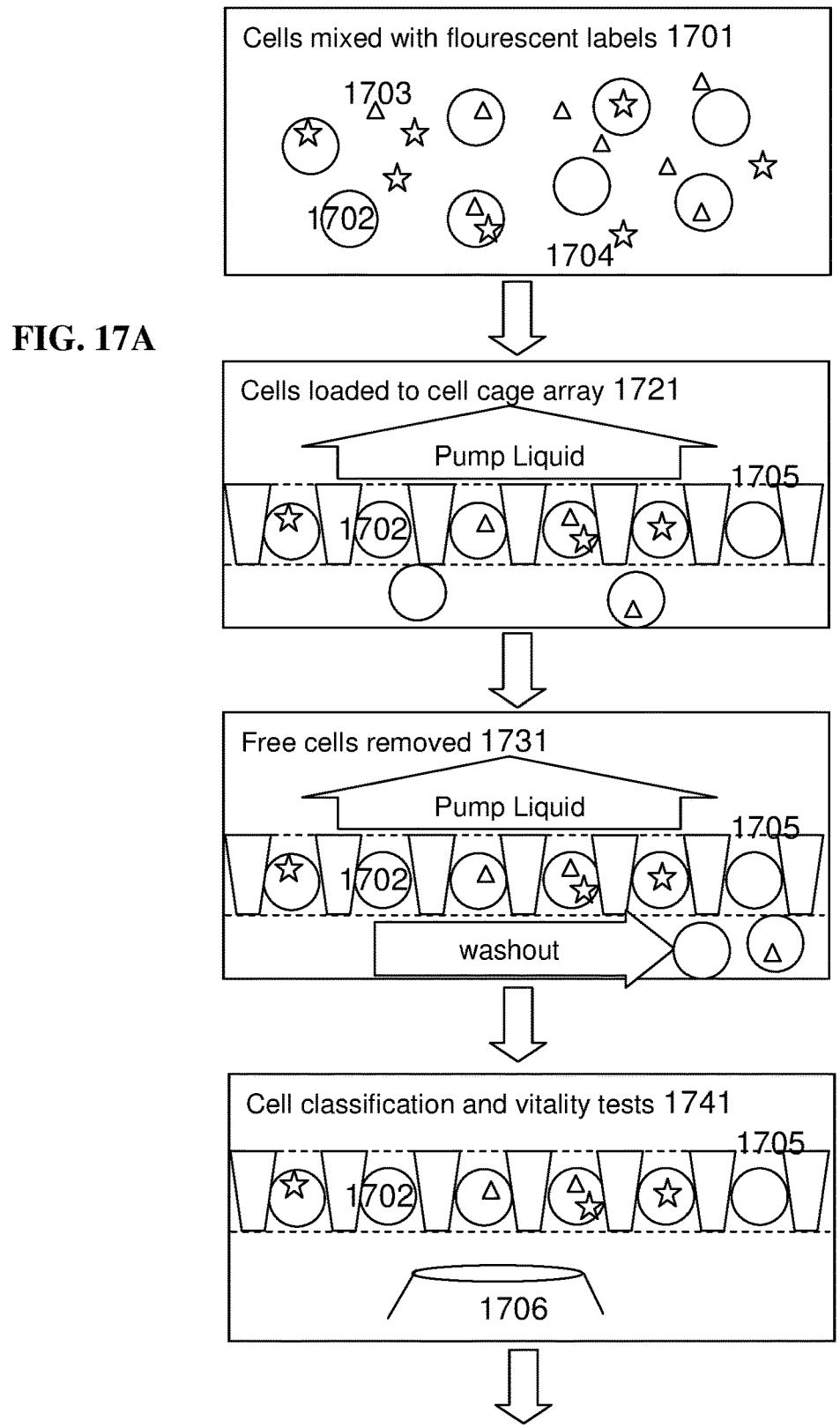
FIG. 17A is a schematic illustration of a cross sectional view of a cell reservoir during steps of a first part of cell proliferation in a cage array, according to some embodiments of the invention.
Figure 17B:
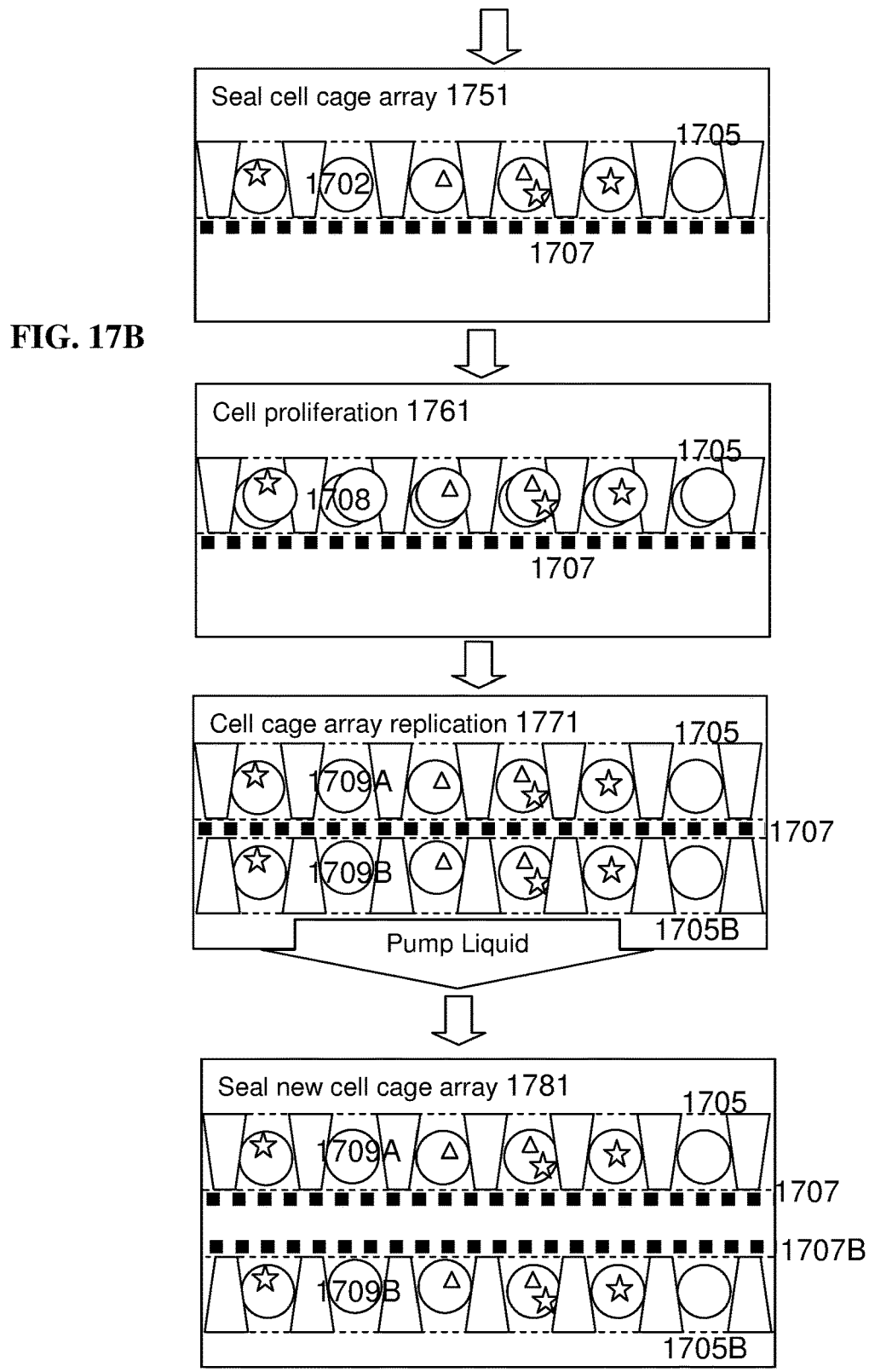
FIG. 17B is a schematic illustration of a cross sectional view of a cell reservoir during steps of a second part of cell proliferation in a cage array, according to some embodiments of the invention.

For example, when creating multiple copies of the same cell may necessitate inducing single cell proliferation, separating individual cells in the emerging sub-clone, and directing each of the cells to a different cage for testing. Reference is now made to FIG. 17A and FIG. 17B, which are schematic illustrations of a cross sectional view of a cell reservoir during steps of a first and second part respectively of cell proliferation in a cell cage array, according to some embodiments of the invention. The cells 1702 in a solution are labeled 1701 with fluorescent labels 1703 and 1704 by adding the fluorescent labels to the solution, and after an absorption time the excess fluorescent labels are washed out. The cells are captured 1721 in a capturing membrane, such as a cell cage array 1705, containing cone-shaped cell cages sized to contain multiple cells. The capturing may be performed by pumping the reservoir liquid from the small aperture side of the cell cage array 1705, such that the fluid flows from the large aperture side into the cell cages drawing cells into the cell cages. Each cone-shaped cell cage may have dimensions of 100 micrometers in height, 70 micrometers for the large radius and 2 micrometers for the small radius, giving a total volume of roughly 130 picoliters. Assuming 1 picoliter as a typical cell volume, this means that in this example embodiment over 100 cells can populate a single cell cage. Once the cell cage array 1705 is detected as having cells in each cell cage according to the flow rate of the pumping action, free cells are removed 1731 by a washout action. The cells may be inspected 1741 using a fluorescent microscope 1706, and their isolation may be completed by sealing 1751 the large aperture of the cell cage array 1705 with a transparent membrane 1707 containing holes slightly smaller than the cells. Cells cannot exit through these holes unless subjected to pumping, such as holes that are at least 1 micrometer smaller than the cell size. Through the transparent membrane, the cells may be monitored during proliferation 1761 until each cage contains the desired number of cells 1708. Necessary medium reagents may be introduced into the reservoir, and the reagents may penetrate the cell cages through the small and large apertures, such as from both sides of the cell cage array 1705. When the sub-clone of each cell is sufficiently large 1708, the cell cage array may 1705 be replicated 1771 by introducing a new capturing membrane 1705B on the other side of the transparent membrane 1707 and optionally pumping liquid towards the new cell cage array 1705B. Alternatively, the cells can migrate by diffusion to the new cell cage array. For example, when the new cell cage array 1705B is coated with gelatin or polylysine at least some of the cells are expected to exit the previous cell cage array 1705 and adhere to the new cell cage array 1705B.

Optionally, the presence of other cells, preloaded in the new cage array 1705B, attracts the cells in the cell cage array 1705 to migrate to the new cage. For example, stromal cells attract stem cells to move towards new cage array 1705B. This leads to cell migration from the original cell cage array 1705 to the new cell cage array 1705B, such that some cells 1709A from each cell cage remain in the original cell cage array 1705 and some cell 1709B migrate to a new corresponding cell cage the new cell cage array 1705B. When pumping is used, the migration may be self-limiting since that as soon as one or more cells 1709B enter each new cell cage, they block the small radius aperture and prevent liquid flow through the cage, thus preventing additional cell migration to that new cell cage. Finally, the new cell cage array 1705B may be sealed 1781 with a second transparent membrane 1707B creating thereby a replica of the original array. This process may be repeated to create as many cell cage array replicas as needed. Tests may be carried out on these new cell cage arrays 1705B, such as drug screenings genomics, transcriptomics, and the like. Optionally or alternatively, the replica can be cultured for further proliferation.

Optionally, the cell array is sealed with a transparent membrane. For example, a transparent membrane seals the cells in the cell cage array to prevent the cell from escaping the cell cages. Optionally, the cell cage array is left open, for example without a sealing transparent membrane.

In many cases, single cell cultures are challenging, as cell to cell signaling is crucial for cell survival and function. For example, stem cells inside the bone marrow develop in small niches containing stromal cells. Embodiments of the present invention enable the benefit of cell to cell chemical exchange through the apertures of the cell cage arrays 1705 and 1705B. These holes are between 1 to 4 micrometers in diameter, thus allowing diffusion of cytokines, hormones, intercellular factors, and the like, needed for cell survival and function inside the cell cages. For example, the sealed cell cage array 1705B may be placed in a reservoir containing a large cell population outside the cell cage array 1705B that exchanges chemicals with the isolated cells through the apertures of the cell cages.

Optionally, supporting cells occupy the cell cages prior to introducing the cells for proliferation. For example, are transferred to the cell cages of the array by diffusion and adhesion to a coated cell cage prior to introduction of the cells to be proliferated to the cell cages by a pumping action.

Optionally, each cell cage has two or more small apertures, such that more than one cell is captured inside each cell cage to investigate the development of a small group of cells. Optionally, the small group of cells are identical cells. Optionally, the small group of cells are different cells. For example, the membrane of FIG. 1C may be modified to have two or more holes between 1 and 4 micrometers in diameter each, one hole for each cell required in the group. In this example, pumping liquid through the membrane may result in capturing a number of cells inside a single cell cage.

Optionally, multiple identical pairs of cells are tested. For example, cells A are placed one in each cell cage of Array A and cells B are placed one in each cell cage of Array B. Array A may be placed against Array B and cells A may be pumped one each into the cell cages of Array B, resulting in one cell A and one cell B in each cell cage of Array B.

The flowchart and block diagrams in the Figures illustrate the architecture, functionality, and operation of possible implementations of systems, methods and devices according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant cytometric methods will be developed and the scope of the term cytometric analysis is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only when the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents, and patent applications mentioned in this specification are herein incorporated in their entirety by reference into the specification, to the same extent as when each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An apparatus for isolation of cells from a liquid medium for cytometric analysis, comprising:
   a cell cage array that comprises a plurality of cell cages, each cell cage comprising a large opening that opens to a cell reservoir, a cell enclosure and at least one small opening adjacent and linking to an enclosed reservoir;
   a liquid medium pump configured to draw liquid medium, comprising a cell suspension, from said cell reservoir to thereby cause liquid to flow from said cell reservoir through cell cages of said cell cage array and to said enclosed reservoir;
   a mechanical element configured to push said cell cage array against a gel layer, thereby said gel layer forming a contiguous barrier to said large openings, to thereby isolate a cell contained in said cell enclosure; and
   wherein said large opening has dimensions large enough for a cell to enter said cell cage, and said at least one small opening has dimensions smaller than said cell, prohibiting said cell from exiting said cell cage into said enclosed reservoir.

2. The apparatus of claim 1, wherein said cell cage array is detachable from said apparatus and wherein said cell cage array is a single-use cell cage array.

3. The apparatus of claim 1, wherein said apparatus further comprises:
at least one first electrode, in electric contact with said liquid medium in said cell reservoir;
a semipermeable membrane between said enclosed reservoir and an ion reservoir;
said ion reservoir containing an ionic fluid; and
at least one second electrode, in electric contact with said ionic fluid, such that a current flowing between said at least one first and second electrodes inject ions into said cell cages.

4. The apparatus of claim 3, wherein said semipermeable membrane is selected from the list consisting of a cation exchange membrane (CEM), a charge mosaic membrane (CMM), a bipolar membrane (BPM), an anion exchange membrane (AEM), an alkali anion exchange membrane (AAEM), and a proton exchange membrane (PEM).

5. The apparatus of claim 3, wherein said at least one first electrode is in electric contact with said liquid medium on one side of said enclosed reservoir, and said second electrode is in electric contact with said liquid medium on an opposite side of said enclosed reservoir, such that ion injection into said cell cages is by diffusion.

6. The apparatus of claim 1, wherein each of said cell enclosures have internal dimensions so that at least one cell fits in each cell cage.

7. The apparatus of claim 6, wherein said cell has a dimension between 1 to 30 micrometers, said cell enclosures have a diameter between 10% to 90% larger than said cell dimension, said large opening has dimensions between 10% to 90% larger than said cell dimension, and said at least one small opening has dimensions between 10% to 90% of said cell dimension.

8. The apparatus of claim 1, wherein said cell enclosures have internal dimensions so that a plurality of cells fit in each said cell cage, wherein said at least one small opening is a plurality of small openings.

9. The apparatus of claim 1, wherein said cell enclosures have an internal shape of a target cell to isolate.

10. The apparatus of claim 1, wherein said cell enclosures have an internal cylindrical shape.

11. The apparatus of claim 1, wherein said cell enclosures have an internal conical shape.

12. The apparatus of claim 1, wherein said cell enclosures have an internal hemispherical shape.

13. The apparatus of claim 1, wherein said cell enclosures have internal dimensions large enough to fit a plurality of individual cells.

14. The apparatus of claim 13, wherein said individual cell has a dimension between 1 to 30 micrometers, said plurality of individual cells comprises N cells, said cell enclosures have a diameter between 10% to 90% larger than said individual cell dimension multiplied by said N cells, said large opening has dimensions between 10% to 90% larger than said individual cell dimension multiplied by said N cells, and said at least one small opening has dimensions between 10% to 90% of said individual cell dimension.

15. The apparatus of claim 1, wherein said liquid medium pump is selected from the list consisting of an electrical pump, a micropump, a manual syringe with an attached caliper, an automatic programmable syringe, a computerized syringe, a syringe driver, a syringe pump, a programmable syringe pump, a media dispenser, an inductive pump, a pressure injection cell dispenser, a peristaltic pump, and an infusion pump.

16. The apparatus of claim 1, wherein between said cell cage array and said enclosed reservoir there is an array support structure, wherein said array support structure maintains said cell cage array in a substantially flat plane.

17. The apparatus of claim 1, wherein said cell cage array is visible through an opaque window in said apparatus.

18. The apparatus of claim 1, wherein said cell cage array further comprises attached antibodies.

19. The apparatus of claim 1, wherein said gel layer further comprises attached antibodies.

20. The apparatus of claim 1, wherein said apparatus further comprises a diffusing gel layer between said cell cage array and said enclosed reservoir.

21. The apparatus of claim 1, wherein said apparatus further comprises an adsorbing layer adjacent to said gel layer, and said adsorbing layer comprises a material selected from the list consisting of nitrocellulose, polyvinylidene difluoride (PVDF) and low fluorescence PVDF.

22. The apparatus of claim 1, wherein said gel layer is composed of any from the list of agarose, acrylamide, and bisacrylamide mixtures.

23. The apparatus of claim 1, wherein said mechanical element is selected from the list consisting of a screw, a level, a step motor, a computerized step motor, linear actuator, and computerized linear actuator.

24. The apparatus of claim 1, wherein said apparatus is a computerized apparatus comprising at least one user interface, at least one component interface, and at least one processing unit capable of controlling at least one component.

* * * * *